United States Patent
Cheng et al.

(10) Patent No.: US 6,238,902 B1
(45) Date of Patent: May 29, 2001

(54) PROTEIN TYROSINE PHOSPHATASES

(75) Inventors: Jill Cheng, Burlingame; Laurence A. Lasky, Sausalito, both of CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 08/821,278

(22) Filed: Mar. 20, 1997

Related U.S. Application Data

(63) Continuation of application No. 08/620,526, filed on Mar. 22, 1996, now abandoned.
(60) Provisional application No. 60/041,602, filed on Mar. 22, 1996.

(51) Int. Cl.[7] .................................................. C12N 9/16
(52) U.S. Cl. .......................... 435/196; 435/377; 435/325
(58) Field of Search ................................ 435/196, 377, 435/325

(56) References Cited

FOREIGN PATENT DOCUMENTS

WO 91/13989    9/1991  (WO).

OTHER PUBLICATIONS

Naeve et al. "Accuracy of automated DNA sequencing: a multi–laboratory comparison of sequencing results" Biotechniques, 1995, vol. 19, No. 3, pp. 448–453, Sep. 1, 1995.*
Melkerson–Watson et al. *J. Immun.*, 153:2004–2013, 1994.*
Ali et al., "PTP1D is a positive regulator of the prolactin signal leading to beta–protein promoter activation" *EMBO Journal* 15(1):135–142 (1996).
Banville et al., "Human protein tyrosine phosphatase 1C (PTPN6) gene structure: alterase as usage and exon skipping generate multiple transcripts" *Genomics* 27(1):165–173 (1995).
Baumhueter et al., "Binding of L–selectin to the vascular sialomucin CD34" *Science* 262:436–438 (1993).
Brady–Kalnay and Tonks, "Protein tyrosine phosphatases as adhesion receptors" *Curr. Opin. Cell. Biol.* 7(5):650–657 (1995).
Charest et al., "Murine protein tyrosine phosphatase–PEST, a stable cytosolic protein tyrosine phosphatase" *Biochemical Journal* 308(2):425–432 (1995).
Darnell et al., "Jak–STAT Pathways and Transcriptional Activation in Response to IFNs and Other Extracellular Signaling Proteins" *Science* 264(5164):1415–1421 (1994).
Deryugina and Muller–Sieburg, "Stromal Cells in Long–Term Cultures: Keys to the Elucidation of Hematopoietic Development?" *Crit. Rev. in Immunol.* 13(2):115–150 (1993).
Fantl et al., "Signalling by Receptor Tyrosine Kinases" *Annual Review in Biochemistry* 62:453–481 (1993).

Fannie et al., "CD34+ endothelial cell lines derived from murine yolk sac induce the proliferation and differentiation of yolk sac CD34+ hematopoietic progenitors" *Blood* 86(12):4454–4467 (1995).
Flores et al., "Nuclear localization of the PEP protein tyrosine phosphatase" *Mol. Cell. Bil.* 14(7):4938–4946 (1994).
Garton and Tonks, "PTP–PEST: a protein tyrosine phosphatase regulated by serine phosphorylation" *EMBO Journal* 13(16):3763–3771 (1994).
Gautier et al., "cdc25 is a specific tyrosine phosphatase that directly activates p34cdc2" *Cell* 67(1):197–211 (1991).
Habib et al., "Activators of protein kinase C stimulate association of Shc and the PEST tyrosine phosphatase" *Journal of Biological Chemistry* 269(41):25243–6 (1994).
Heim et al., "Contribution of STAT SH2 groups to specific interferon signaling by the Jak–STAT pathway" *Science* 267(5202):1347–9 (1995).
Ihle et al., "Signaling through the hematopoietic cytokine receptors" *Annu. Rev. Immunol.* 13:369–398 (1995).
Jia et al., "Structural basis for phosphotyrosine peptide recognition by protein tyrosine phosphatase 1B" *Science* 268(5218):1754–1758 (1995).
King et al., "Isolation and characterization of a uniquely regulated threonine, serine, tyrosine phosphatase (TYP 1) which inactivates ERK2 and p53ink" *Oncogene* 11:2553–2563 (1995).
Klingmuller et al., "Specific recruitment of SH–PTP1 to the erythropoietin causes inactivation of JAK2 and termination of proliferative signals" *Cell* 80(5):729–738 (1995).
Krause et al., "Characterization of murine CD34, a marker for hematopoietic progenitor and stem cells" *Blood* 84(3):691–701 (1994).
Kulas et al., "The transmembrane protein–tyrosine phosphatase CD45 is associated with decreased insulin receptor signaling" *Journal of Biological Chemistry* 271(2):755–760 (1996).
Kulas et al., "The transmembrane protein–tyrosine phosphatase LAR modulates signaling by multiple receptor tyrosine kinases" *Journal of Biological Chemistry* 271(2):748–754 (1996).

(List continued on next page.)

Primary Examiner—Ponnathapu Achutamurthy
Assistant Examiner—Bradley S. Mayhew
(74) Attorney, Agent, or Firm—Knobbe, Martens, Olson & Bear, LLP

(57) ABSTRACT

This invention concerns new non-receptor protein tyrosine phosphatases of the hematopoietic stem cells (PTP HSC). The invention specifically concerns native murine and human PTP HSCs, their analogs in other mammals, and their functional derivatives. The invention further relates to nucleic acid encoding these proteins, vectors containing and capable of expressing such nucleic acid, and recombinant host cells transformed with such nucleic acid. Assays for identifying agonists and antagonists of the native PTP HSCs, methods for expansion of undifferentiated stem cells, and methods for the induction of stem cell differentiation are also within the scope of the invention.

3 Claims, 10 Drawing Sheets

OTHER PUBLICATIONS

Matthews et al., "Characterization of hematopoietic intracellular protein tyrosine phosphatases: description of a phosphatase containing an SH2 domain and another enriched in proline–, glutamic acid–, serine–, and threonine–rich sequences" *Molecular & Cellular Biology* 12(5):2396–2405 (1992).

McCulloch and Siminovitch, "Involvement of the protein tyrosine phosphatase ptpic in cellular physiology, autoimmunity and oncogenesis" *Adv. Exp. Med. Biol.* 365:245–254 (1994).

Morrison et al., "The biology of hematopoietic stem cells" *Ann. Rev. Cell Dev. Biol.* 11:35–71 (1995).

Orkin, S.H., "Hematopoiesis: How does it happen?" *Curr. Open. Cell. Biol.* 7(6):870–877 (1995).

Paulson and Bernstein, "Receptor tyrosine kinases and the regulation of hematopoiesis" *Semin Immunol.* 7(4):267–277 (1995).

Peters et al., "Ex Vivo expansion of murine marrow cells with interleukin–3 (IL–3), IL–6, IL–11, and stem cell factor leads to impaired engraftment in irradiated hosts" *Blood* 87(1):30–37 (1996).

Shuai et al., "A single phosphotyrosine residue of Stat91 required for gene activation by interferon–gamma" *Science* 261(5129):1744–1746 (1993).

Shultz et al., "Mutations at the murine motheaten locus are within the hematopoietic cell protein–tyrosine phosphatase (Hcph) gene" *Cell* 73:1445–1454 (1993).

Spangrude et al., "Purification and characterization of mouse hematopoietic stem cells" *Science* 241:58–62 (1988).

Sun and Tonks, "The coordinated action of protein tyrosine phosphatases and kinases in cell signaling" *Trends Biochem. Sci.* 19(11):480–485 (1994).

Takekawa et al., "Cloning and characterization of a human cDNA encoding a novel putative cytoplasmic protein–tyrosine–phosphatase" *Biochem. & Biophys. Res. Comm.* 189(2):1223–1230 (1992).

Uchida et al., "Rapid and sustained hematopoietic recovery in lethally irradiated mice transplanted with purified Thy–1.1lo Lin– Sca–1+ hematopoietic stem cells" *Blood* 83(12):3758–3779 (1994).

Walton and Dixon, "Protein tyrosine phosphatases" *Ann. Rev. Biochem.* 62:101–120 (1993).

Yang et al., "Cloning and expression of PTP–Pest. A novel, human nontransmembrane protein tyrosine phosphatase" *Journal of Biological Chemistry* 268(23):17650 (1993).

Zeigler et al., "Cellular and Molecular Characterization of the Role of the FLK–2/FLT–3 Receptor Tyrosine Kinase in Hematopoietic Stem Cells" *Blood* 84(8):2422–2430 (1994).

Cheng et al., "A novel protein tyrosine phosphatase expressed in lin lo CD34 hi Sca hi hematopoietic progenitor cells" *Blood* 88(4):1156–1167 (1996).

Dosil et al., "Cloning and characterization of fetal liver phosphatase 1, a nuclear protein tyosine phosphatase isolated from hematopoietic stem cells" *Blood* 88(12):4510–4525 (1996).

Kim et al., "Characterization of the PEST family protein tyrosine phosphatase BDP1" *Oncogene* 13:2275–2279 (1996).

Yi et al., "Identification of novel protein tyrosine phosphatases of Hematopoietic cells by polymerase chain reaction amplification" *Blood* 78(9):2222–2228 (1991).

Dosil, M. et al., "Cloning and characterization of a nuclear protein tyrosine phosphatase isolated from mouse hematopoietic stem cells" *Blood* 86(10):Suppl. 1, 307a (1995).

Lemischka, I.R., ""The development and molecular properties of hematopoietic stem cells" in: Leukemia and Lymphoma" 18th Symp. of the Int'l Assoc. for Competitive Res. on Leukemia and Related Diseases (Kyoto, Japan) p. 35 (1995).

Schumann, G. et al., "Selective expression of protein tyrosine phosphatases in early human hematopoietic progenitor cells" *J. Cell Biochem.* Suppl. 21A:371 (1995).

* cited by examiner

```
  1 CTCAGAGCGG GTCGCAGCAT GAGTCGCCAT ACGGACTTGG TGAGGAGCTT CTTGGAGCAG
  1                       M  S  R  H  T  D  L  V  R  S  F  L  E  Q

61 CTGGAGGCCC GGGACTACCG GGAGGGGGCA ATCCTCGCTC GTGAGTTCAG CGACATTAAG
 15 L  E  A  R  D  Y  R  E  G  A  I  L  A  R  E  F  S  D  I  K

121 GCCCGCTCAG TGGCCTGGAA GTCTGAAGGT GTGTGTTCCA CTAAAGCCGG CAGTCGGCTT
 35 A  R  S  V  A  W  K  S  E  G  V  C  S  T  K  A  G  S  R  L

181 GGGAACACGA ACAAGAACCG CTACAAAGAT GTGGTAGCAT ATGATGAGAC AAGAGTCATC
 55 G  N  T  N  K  N  R  Y  K  D  V  V  A  Y  D  E  T  R  V  I

241 CTTTCCCTGC TCCAAGAGGA GGGACATGGA GATTACATCA ATGCCAACTT CATCCGGGGC
 75 L  S  L  L  Q  E  E  G  H  G  D  Y  I  N  A  N  F  I  R  G

301 ATAGATGGAA GCCAGGCCTA CATTGCGACG CAAGGACCCC TGCCTCACAC ACTGTTGGAC
 95 I  D  G  S  Q  A  Y  I  A  T  Q  G  P  L  P  H  T  L  L  D

361 TTCTGGCGCC TGGTTTGGGA GTTTGGGGTC AAGGTAATCC TGATGGCCTG TCAAGAGACA
115 F  W  R  L  V  W  E  F  G  V  K  V  I  L  M  A  C  Q  E  T

421 GAAAATGGAC GGAGGAAGTG TGAACGCTAC TGGGCCCGGG AGCAGGAGCC TCTAAAGGCT
135 E  N  G  R  R  K  C  E  R  Y  W  A  R  E  Q  E  P  L  K  A

481 GGGCCTTTCT GCATCACCCT GACAAAGGAG ACAACACTGA ATGCAGACAT CACTCTCAGG
155 G  P  F  C  I  T  L  T  K  E  T  T  L  N  A  D  I  T  L  R

541 ACCCTCCAGG TTACATTCCA GAAGGAATTC CGCTCTGTGC ACCAGCTACA GTATATGTCC
175 T  L  Q  V  T  F  Q  K  E  F  R  S  V  H  Q  L  Q  Y  M  S

601 TGGCCAGACC ACGGGGTTCC CAGCAGTTCT GATCACATTC TCACCATGGT GGAGGAGGCC
195 W  P  D  H  G  V  P  S  S  S  D  H  I  L  T  M  V  E  E  A
                                                     *
661 CGCTGCCTCC AAGGGCTTGG ACCTGGACCC CTCTGTGTCC ACTGCAGTGC TGGCTGCGGA
215 R  C  L  Q  G  L  G  P  G  P  L  C  V  H  C  S  A  G  C  G
```

FIG. 1A

```
721  CGAACAGGTG  TCCTGTGCGC  TGTTGACTAT  GTGAGGCAGT  TGCTGCTGAC  CCAGACAATC
235  R  T  G  V    L  C  A    V  D  Y    V  R  Q  L    L  L  T    Q  T  I

781  CCTCCCAACT  TCAGTCTCTT  CCAAGTGGTC  CTGGAGATGC  GGAAACAGCG  GCCTGCAGCA
255  P  P  N  F    S  L  F    Q  V  V    L  E  M  R    K  Q  R    P  A  A

841  GTGCAGACAG  AGGAGCAGTA  CAGGTTCCTG  TACCACACAG  TGGCTCAGCT  ATTCTCCCGC
275  V  Q  T  E    E  Q  Y    R  F  L    Y  H  T  V    A  Q  L    F  S  R

901  ACTCTCCAGG  ACACCAGCCC  CCACTACCAG  AACCTCAAGG  AGAACTGCGC  TCCAATCTGC
295  T  L  Q  D    T  S  P    H  Y  Q    N  L  K  E    N  C  A    [P] I  C

961  AAGGAAGCCT  TCTCCCTCAG  GACCTCCTCA  GCCCTGCCTG  CCACATCCCG  GCCACCAGGA
315  K  E  A  F   [S] L  R   [T][S][S]   A  L [P] A  [T][S] R    [P][P] G

1021 GGGGTTCTCA  GGAGCATCTC  GGTGCCTGCG  CCCCCGACCC  TCCCCATGGC  TGACACTTAC
335  G  V  L  R  [S] I [S]   V [P] A    [P][P][T] L    [P] M  A    D [T] Y

1081 GCTGTGGTGC  AGAAGCGTGG  CGCTTCGGCG  GGCACAGGGC  CGGGGCCGCG  GGCGCCCACC
355  A  V  V  Q    K  R  G    A [S] A    G [T] G [P]   G [P] R    A [P][T]

1141 AGCACGGACA  CCCCGATCTA  CAGCCAGGTG  GCTCCACGTG  CCCAGCGACC  GGTGGCACAC
375 [S][T] D [T]  [P] I  Y   [S] Q  V    A [P] R  A    Q  R [P]    V  A  H

1201 ACGGAGGACG  CACAGGGGAC  AACGGCACTG  CGCCGAGTTC  CTGCGGACCA  AAACTCTTCC
395 [T] E  D  A    Q  G [T]  [T] A  L    R  R  V [P]   A  D  Q    N [S][S]

1261 GGGCCTGATG  CCTACGAAGA  AGTAACAGAT  GGAGCACAGA  CTGGAGGGCT  AGGCTTCAAC
415  G [P] D  A    Y  E  E    V [T] D    G  A  P [T]   G  G  L    G  F  N

1321 TTGCGCATCG  GAAGGCCCAA  AGGGCCCCGG  GATCCTCCAG  CAGAGTGGAC  ACGGGTGTAA
435  L  R  I  G    R  P  K    G  P  R    D  P  P  A    E  W  T    R  V  Q

1381 CGAGTGCTGT  GCCAGTTATA  GCCTGCCACT  CGGTGGTGGC  TGGACTCCTG  GAACCACCAT

1441 ACTGCTGTGC  AGTGTGTTAT  GTATGAGTGG  GACTTGTGGG  CCTGATTCAA  AATAAAAGTT

1501 TCTCAGGGCA  GAAAAAAAAA  AAAAAAAAA
```

```
GCGCGGGGCG GCCGGGAGGG GGCAGTCCTC GCCGGCGAGT TCAGCGACAT  50

CCAGGCCTGC TCGGCCGCCT GGAAGGCTGA CGGCGTGTGC TCCACCGTGG 100

CCGGCAGTCG GCCAGAGAAC GTGAGGAAGA ACCGCTACAA AGACGTGCTG 150

CCTTATGATC AGACGCGAGT AATCCTCTCC CTGCTCCAGG AAGAGGGACA 200

CAGCGACTAC ATTAATGGCA ACTTCATCCG GGGCGTGGAT GGAAGCCTGG 250

CCTACATTGC CACGCAAGGA CCCTTGCCTC ACACCCTGCT AGACTTCTGG 300

AGACTGGTCT GGGAGTTTGG GGTCAAGGTG ATCCTGATGG CCTGTCGAGA 350

GATAGAGAAT GGGCGGAAAA GGTGTGAGCG GTACTGGGCC CAGGAGCAGG 400

AGCCACTGCA GACTGGGCTT TTCTGCATCA CTCTGATAAA GGAGAAGTGG 450

CTGAATGAGG ACATCA 466
```

FIG.8A

```
Ala Arg Gly Gly Arg Glu Gly Ala Val Leu Ala Gly Glu Phe Ser
 1               5                   10                  15
Asp Ile Gln Ala Cys Ser Ala Ala Trp Lys Ala Asp Gly Val Cys
                20                  25                  30
Ser Thr Val Ala Gly Ser Arg Pro Glu Asn Val Arg Lys Asn Arg
                35                  40                  45
Tyr Lys Asp Val Leu Pro Tyr Asp Gln Thr Arg Val Ile Leu Ser
                50                  55                  60
Leu Leu Gln Glu Glu Gly His Ser Asp Tyr Ile Asn Gly Asn Phe
                65                  70                  75
Ile Arg Gly Val Asp Gly Ser Leu Ala Tyr Ile Ala Thr Gln Gly
                80                  85                  90
Pro Leu Pro His Thr Leu Leu Asp Phe Trp Arg Leu Val Trp Glu
                95                  100                 105
Phe Gly Val Lys Val Ile Leu Met Ala Cys Arg Glu Ile Glu Asn
                110                 115                 120
Gly Arg Lys Arg Cys Glu Arg Tyr Trp Ala Gln Glu Gln Glu Pro
                125                 130                 135
Leu Gln Thr Gly Leu Phe Cys Ile Thr Leu Ile Lys Glu Lys Trp
                140                 145                 150
Leu Asn Glu Asp Ile
                155
```

FIG.8B

PROTEIN TYROSINE PHOSPHATASES

This is a non-provisional application filed under 37 CFR 1.53(b)(1), claiming priority under U.S.C. Section 119(e) claims benefit of provisional Application No. 60/041,602 filed on Mar. 22, 1996 and a cont. of Ser. No. 08/620,526 filed Mar. 22, 1996, now abandoned.

FIELD OF THE INVENTION

The present invention concerns novel protein tyrosine phosphatases. More particularly, the invention concerns non-receptor protein tyrosine phosphatases of hematopoietic stem cells (PTP HSC's).

BACKGROUND OF THE INVENTION

The ability of the hematopoietic stem cell to function as a source of committed progenitors throughout the lifetime of the organism is, at present, a poorly understood phenomenon. The major characteristic of the hematopoietic stem cell is its ability to self renew in the absence of differentiation (Morrison et al., *Ann. Rev. Cell Dev. Biol.*, 11, 35–71 [1995]). This self renewal phenomenon is especially remarkable in light of the fact that the hematopoietic stroma, which is in close physical contact with the stem cell, is known to be a source that is rich in factors which mediate the growth and differentiation of hematopoietic progenitors (Deryugina and Muller-Sieberg, *Crit. Rev. in Immunol.* 13(2), 115–150 [1993]). For example, a recent PCR analysis of hematopoietically active endothelial cell stromal lines derived from the murine yolk sac revealed that these cells produced a plethora of growth and differentiation factors including stem cell factor, FLT 3 ligand, M-CSF, LIF and IL-6 (Fennie et al., *Blood* 86(12), 4454–4467 [1995]). Such growth factors, in addition to many others, are known to induce the expansion and differentiation of stem cells, and these endothelial cell lines induced a rapid expansion and differentiation of embryonic hematopoietic stem cells along the myeloid pathway, although very early progenitor cells are also amplified by these stromal cells (C. Fennie and L. Lasky—unpublished data). It has also been shown that incubation of highly purified stem cell populations in the presence of various purified hematopoietic growth factors induces differentiation with subsequent loss of the cells' ability to competitively repopulate the hematopoietic compartment of lethally irradiated animals, consistent with the induction of terminal differentiation (Peters et al., *Blood* 87(1): 30–37 [1996]). Thus, the stem cell, whether in an embryonic or adult stromal environment, must maintain an undifferentiated state in spite of the fact that it is being exposed to a variety such maturation factors (Deryugina and Muller-Sieberg, supra).

Although the hematopoietic growth factors are very diverse both structurally and functionally, they are all believed to play a role in mediating protein phosphorylation (Paulson and Bernstein, *Semin Immunol.* 7(4), 267–77 [1995]). This protein modification can occur via direct means, such as in the cases of the stem cell factor and FLT-3 receptors, both of which have intrinsic tyrosine kinase activity, or via indirect means, as is the case of the hematopoietic/cytokine growth factor receptors for, for example, IL-3, EPO and TPO. In the case of the hematopoietic/cytokine growth factor receptors, tyrosine phosphorylation is indirectly accomplished by the activation of the JAK kinases, which occurs after growth factor mediated receptor dimerization (Ihle et al., *Annu. Rev. Immunol.* 13, 369–398 [1995]). In both cases, diverse complex pathways of protein phosphorylation are stimulated upon receptor binding. The intrinsic tyrosine kinase receptors mediate their signals via an elaborate series of tyrosine phosphorylation events which ultimately activate the RAS signaling pathway (Fantl et al., *Ann. Rev. Biochem.* 62, 453–481 [1993]). This pathway eventually leads to the activation of the serine/threonine specific MAP kinase pathway which results in transcriptional activation. In contrast to this intricate pathway, hematopoietic growth factor-induced receptor dimerization mediates more direct activation events. Thus, the stimulation of the JAK kinases by receptor binding leads to the tyrosine phosphorylation and subsequent dimerization of various STAT proteins. These activated STAT proteins than migrate to the nucleus, bind to STAT responsive sites in the nuclear DNA and induce transcription of differentiation and growth specific genes. Thus, a major effect of the growth factors produced by the hematopoietic stroma is to mediate the activation of various cellular pathways by protein phosphorylation.

The regulation of protein tyrosine phosphorylation is accomplished by a balance between protein tyrosine kinases and protein tyrosine phosphatases (PTPs) (Walton and Dixon, *Ann. Rev. Biochem.* 62, 101–120 [1993]; Sun and Tonks, *Trends Biochem. Sci.*, 19(11), 480–485 [1994]). All PTPs contain a phosphatase domain including a subset of highly conserved amino acids, and a recent crystal structure analysis of PTP 1B complexed with a tyrosine phosphorylated peptide revealed that many of these conserved residues are involved with substrate recognition and tyrosine dephosphorylation (Jia et al., *Science* 268(5218), 1754–1758 [1995]). PTPs fall into two general categories: receptor type and non-receptor type. The receptor type PTPs have variously sized extracellular domains and, generally, two intracellular phosphatase domains Walton and Doxin, supra; Sun and Tonks, supra. The extracellular domains often contain a number of motifs that are generally utilized in cell adhesion including immunoglobulin domains and fibronectin-like regions. Many of these PTPs appear to function as homotypic and heterotypic sensors of the extracellular space, and they have been hypothesized to play roles in contact inhibition, cell guidance and other intercellular functions (Brady-Kalnay and Tonks, *Curr. Opin. Cell. Biol.* 7(5), 650–657 [1995]). The non-receptor PTPs are generally intracellular enzymes. They have various cellular localizations, depending upon the types of domains they contain, and some of the enzymes contain SH2 motifs which allow them to interact intimately with phosphotyrosine residues. While many of the non-receptor PTPs are in various cytoplasmic locations, a small number of these enzymes are found in the nucleus Flores et al., *Mol. Cell. Biol.* 14(7), 4938–46 [1994]). Many non-receptor PTPs appear to function as both activators as well as inhibitors of diverse tyrosine phosphorylated proteins. A subset appear to play important roles in hematopoiesis. For example, the motheaten mouse, which has a phenotype of lethal myeloid amplification and inflammation, has been found to have a mutation in the PTP 1C gene Shultz et al., *Cell* 73(7), 1445–54 [1993]; McCulloch and Siminovitch, *Adv. Exp. Med. Biol.* 365, 245–54 [1994]). In addition, the level of tyrosine phosphorylation of the EPO receptor, as well as the level of receptor activation, appears to be in part controlled by the PTP 1C enzyme as well Klingmuller et al., *Cell* 80(5), 729–38 [1995]). However, while these examples, as well as others, highlight the potential importance of the PTPs, very little is known regarding the physiological importance of these enzymes.

SUMMARY OF THE INVENTION

We have hypothesized that one mechanism by which the undifferentiated state of the stem cell might be maintained is by the dephosphorylation of tyrosine phosphorylated proteins by PTPs. In order to examine this possibility, we have analyzed a large number of PTPs from a very primitive embryonic hematopoietic cell population using consensus PCR. From this population we have cloned a novel intracellular PTP which has many of the characteristics, including down-regulation of the transcript as the hematopoietic stem cells differentiate, which might be expected from a PTP involved with the control of differentiation signals such as those induced by hematopoetic growth factors. We have designated this novel PTP as the "PTP of hematopoietic stem cells", which will be referred to hereafter as "PTP HSC."

Accordingly, the present invention concerns an isolated non-receptor protein tyrosine phosphatase of hematopoietic stem cells (PTP HSC), which (1) is expressed predominantly in early hematopoietic stem/progenitor cells;

(2) predominantly lacks expression in adult tissues;

(3) comprises an N-terminal tyrosine phosphatase domain, followed by a region rich in serine, threonine, and proline, and a carboxy terminal region of about 15 to 25 amino acids rich in basic amino acid residues; and (4) is capable of tyrosine dephosphorylation in hematopoietic stem cells or progenitor cells.

This novel PTP preferably downregulates STAT activation. A preferred group of the PTP HSC proteins of the present invention includes a protein comprising the amino acid sequence shown in FIG. 1 (SEQ. ID. NO:2); a protein comprising the amino acid sequence shown in FIG. 8B (SEQ. ID. NO: 17), a further mammalian homologue of either protein; and derivatives of the foregoing proteins retaining the ability of tyrosine dephosphorylation in hematopoietic stem cells or progenitor cells.

The PTP HSCs, including derivatives (e.g. amino acid sequence variants) of the native proteins, preferably have an active N-terminal tyrosine phosphatase domain, retaining a serine residue at a position corresponding to amino acid position 37 in FIG. 1, and retaining an active site cysteine residue at a position corresponding to amino acid position 229 in FIG. 1, a region rich in serine, threonine, and proline, and a carboxy-terminal region showing at least about 80% sequence homology with the amino acid sequence between positions 430 and 451 in FIG. 1. Most preferably, such derivatives have at least about 65% overall sequence homology with the amino acid sequence shown in FIG. 1 or FIG. 8B, and retain the ability of tyrosine dephosphorylation in hematopoietic stem cells or progenitor cells.

In another aspect, the present invention concerns agonists and antagonists of PTP HSCs.

In yet another aspect, the invention concerns isolated nucleic acid molecules encoding the PTP HSCs herein.

In a further aspect, the invention concerns vectors comprising nucleic acid encoding the PTP HSCs herein, operably linked to control sequences recognized by a host cell transformed with the vector, and to cells transformed with such vectors.

In a still further aspect of the present invention, there are provided antibodies capable of specific binding to the PTP HSCs of this invention, and hybridoma cell lines producing such antibodies. The antibodies may be agonist antibodies, which stimulate the ability of the native PTP HSCs of the present invention to dephosphorylate tyrosines, or antagonist antibodies, which block this activity.

The present invention further concerns an assay for identifying an antagonist or an agonist of a PTP HSC of the present invention, which comprises contacting the phosphatase domain of the PTP HSC with a candidate antagonist or agonist, and monitoring the ability of the phosphatase domain to dephosphorylate tyrosine residues.

In another embodiment, the invention concerns an assay for identifying an antagonist or agonist of a PTP HSC of the present invention by cultivating a PTP HSC-expressing hematopoietic stem cell line or progenitor cell line in the presence of a candidate antagonist or agonist, and monitoring the differentiation of the progenitor cells.

The invention further concerns a method for the differentiation of undifferentiated malignant hemopoietic (e.g. leukemia) cells, comprising contacting said cells with an antagonist of a PTP HSC of the present invention.

In an additional aspect, the invention concerns a method for the induction of hematopoietic stem cell differentiation, comprising contacting said stem cells with an antagonist of a PTP HSC of the present invention.

In another aspect, the invention concerns a method for expansion undifferentiated hematopoietic stems cells in cell culture, comprising cultivating stem cells in the presence of a PTP HSC of the present invention or an agonist antibody specifically binding a native PTP HSC.

In yet another aspect, the invention concerns a method for the expansion of undifferentiated stem cells in vivo comprising administering to a patient an agonist of PTP HSC of the present invention or an agonist antibody specifically binding a native PTP HSC, and a stem cell growth factor.

BRIEF DESCRIPTION OF THE DRAWINGS

FIGS. 8A and B. Partial DNA and deduced protein sequence of the human PTP HSC cDNA. Illustrated is the partial DNA sequence (FIG. 8A, SEQ ID. NO: 16) and deduced protein sequence FIG. 8B (SEQ. ID. NO: 17) of the human PTP HSC cDNA.

DETAILED DESCRIPTION OF THE INVENTION

A. Definitions

Figure 3:
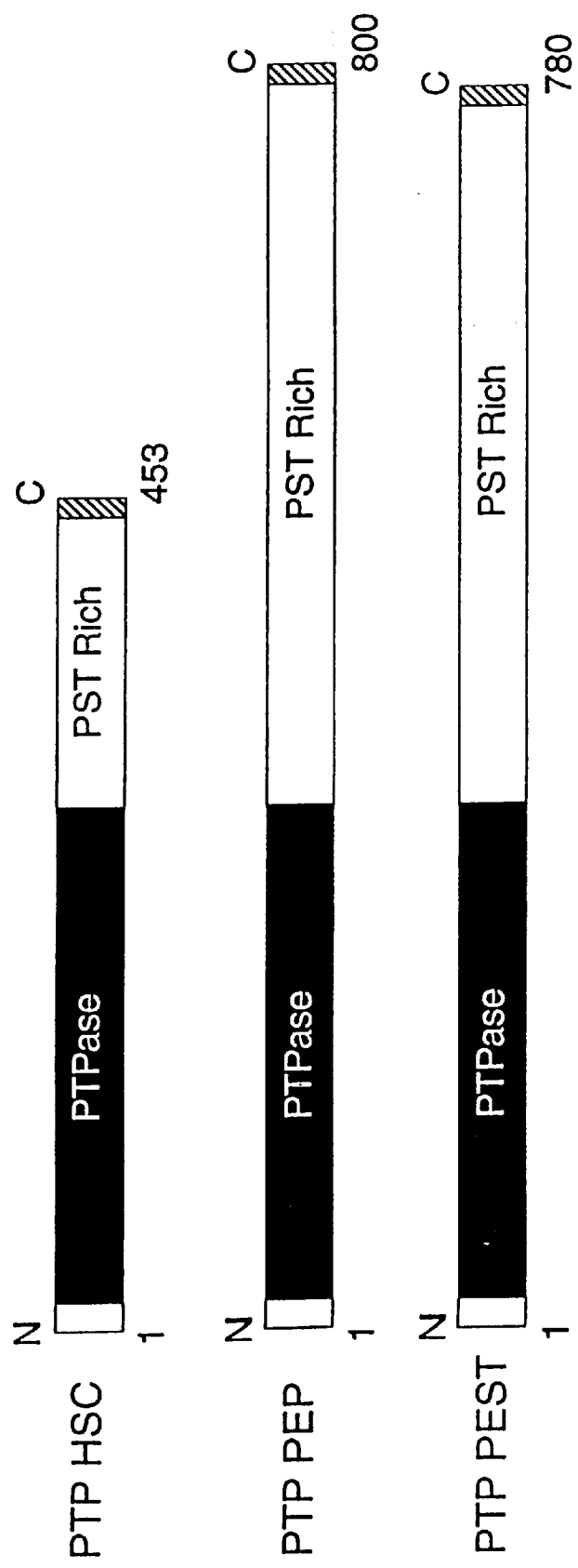
FIG. 3. The PTP PST family. Illustrated are the three so far identified members of this family including the currently described novel PTP (PTP HSC). Shown are the amino terminal PTP domains (black), the P,S,T rich domains, and the carboxy terminal nuclear localization homology (shaded).

The phrases "non-receptor protein tyrosine phosphatase of hematopoietic stem cells", "tyrosine phosphatase of hematopoietic stem cells" and "PTP HSC" are used interchangeably and refer to a native intracellular protein tyrosine phosphatase which (1) is expressed predominantly in early hematopoietic stem and progenitor cells; (2) predominantly lacks expression in adult tissues; (3) comprises an N-terminal tyrosine phosphatase domain, followed by a region rich in serine, threonine, and proline, and a carboxy terminal region of about 15 to 25 amino acids rich in basic amino acid residues; and (4) is capable of tyrosine dephosphorylation in hematopoietic progenitor cells, and functional derivatives of such native tyrosine phosphatase.

The term "native tyrosine phosphatase" in this context refers to a naturally occurring tyrosine phosphatase, having the described properties, of any human or non-human animal species, with or without the initiating methionine, whether purified from native source, synthesized, produced by recombinant DNA technology or by any combination of these and/or other methods. Native PTP HSCs specifically include the native murine and native human HSC proteins (SEQ. ID. NOs: 2 and 17, respectively).

A "functional derivative" of a polypeptide is a compound having a qualitative biological activity in common with the native polypeptide. Thus, a functional derivative of a native PTP HSC polypeptide is a compound that has a qualitative biological activity in common with a native PTP HSC. "Functional derivatives" include, but are not limited to, fragments of native polypeptides from any animal species (including humans), derivatives of native (human and non-human) polypeptides and their fragments, and peptide and non-peptide analogs of native polypeptides, provided that they have a biological activity in common with a respective native polypeptide. "Fragments" comprise regions within the sequence of a mature native polypeptide. The term "derivative" is used to define amino acid sequence variants, and covalent modifications of a native polypeptide. "Non-peptide analogs" are organic compounds which display substantially the same surface as peptide analogs of the native polypeptides. Thus, the non-peptide analogs of the native PTP HSCs of the present invention are organic compounds which display substantially the same surface as peptide analogs of the native PTP HSCs. Such compounds interact with other molecules in a similar fashion as the peptide analogs, and mimic a biological activity of a native PTP HSC of the present invention. The polypeptide functional derivatives of the native PTP HSCs of the present invention preferably have an active N-terminal tyrosine phosphatase domain, retaining a serine residue at a position corresponding to amino acid position 37 in FIGS. 1A and 1B, and retaining an active site cysteine residue at a position corresponding to amino acid position 229 in FIG. 1; a region rich in serine, threonine, and proline; and a carboxy-terminal region showing at least about 80% sequence homology with the amino acid sequence between positions 430 and 451 in FIG. 1. Preferably, such derivatives have at least about 65%, more preferably at least about 75%, even more preferably at least about 85%, most preferably at least about 95% overall sequence homology with the amino acid sequence shown in FIG. 1 (SEQ. ID. NO: 2) or FIG. 8 (SEQ. ID. NO: 17) and retain the ability of tyrosine dephosphorylation in hematopoietic progenitor cells.

The term "biological activity" in the context of the definition of functional derivatives is defined as the possession of at least one adhesive, regulatory or effector function qualitatively in common with a native polypeptide (e.g. PTP HSC). The functional derivatives of the native PTP HSCs of the present invention are unified by their qualitative ability of tyrosine dephosphorylation in hematopoietic progenitor cells. In addition, the functional derivatives of the native PTP HSCs herein preferably are capable of downregulating STAT activation.

The term "agonist" is used to refer to peptide and non-peptide analogs of the native PTP HSCs of the present invention and to antibodies specifically binding such native PTP HSCs provided that they retain the qualitative ability of tyrosine dephosphorylation in hematopoietic progenitor cells.

The term "antagonist" is used to refer to a molecule inhibiting the ability of a PTP HSC of the present invention to dephosphorylate tyrosines. Preferred antagonists essentially completely block tyrosine dephosphorylation caused by a PTP HSC.

"Identity" or "homology" with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Neither N- or C-terminal extensions nor insertions shall be construed as reducing identity or homology. Methods and computer programs for the alignment are well known in the art.

The term "stem cell" is used in the broadest sense to describe cells which are not terminally differentiated and have the ability to divide throughout the lifetime of the organism, yielding some progeny that differentiate and others that remain stem cells, including stem cells of any tissue type, such as the lining of the gut, the epidermal layer of the skin and the blood-forming tissues.

The term "hematopoietic stem cell" is used in the broadest sense to refer to stem cells from which blood cells derive, including pluripotent stem cells, lymphoid and myeloid stem cells.

The term "hematopoietic progenitor cell" refers to the progeny of a pluripotent hematopoietic stem cell which are committed for a particular line of differentiation. These committed progenitor cells are irreversibly determined as ancestors of only one or a few blood cell types, e.g. erythrocytes or granulocytes.

"Hematopoietic growth factors" are growth factors that influence blood cell formation or differentiation in vivo, such as EPO, TPO, IL-3, IL-6, stem cell growth factor, M-CSF, G-CSF, GM-CSF, FTL 3 ligand, LIF, etc., unified by their role in mediating protein phosphorylation. The receptors of these growth factors are either transmembrane tyrosine kinases or are members of the cytokine receptor family.

Ordinarily, the terms "amino acid" and "amino acids" refer to all naturally occurring L-α-amino acids. In some embodiments, however, D-amino acids may be present in the polypeptides or peptides of the present invention in order to facilitate conformational restriction. For example, in order to facilitate disulfide bond formation and stability, a D amino acid cysteine may be provided at one or both termini of a peptide functional derivative or peptide antagonist of the native PTP HSC's of the present invention. The amino acids are identified by either the single-letter or three-letter designations:

| Asp | D | aspartic acid | Ile | I | isoleucine |
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

These amino acids may be classified according to the chemical composition and properties of their side chains. They are broadly classified into two groups, charged and uncharged. Each of these groups is divided into subgroups to classify the amino acids more accurately:

I. Charged Amino Acids
   Acidic Residues: aspartic acid, glutamic acid
   Basic Residues: lysine, arginine, histidine II. Uncharged Amino Acids
   Hydrophilic Residues: serine, threonine, asparagine, glutamine
   Aliphatic Residues: glycine, alanine, valine, leucine, isoleucine
   Non-polar Residues: cysteine, methionine, proline
   Aromatic Residues: phenylalanine, tyrosine, tryptophan The term "amino acid sequence variant" refers to molecules with some differences in their amino acid sequences as compared to a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Insertional variants are those with one or more amino acids inserted immediately adjacent to an amino acid at a particular position in a native sequence. Immediately adjacent to an amino acid means connected to either the α-carboxy or α-amino functional group of the amino acid.

Deletional variants are those with one or more amino acids in the native amino acid sequence removed. Ordinarily, deletional variants will have one or two amino acids deleted in a particular region of the molecule.

"Antibodies (Abs)" and "immunoglobulins (Igs)" are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one and ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., *J. Mol. Biol.* 186, 651–663 [1985]; Novotny and Haber, *Proc. Natl. Acad. Sci. USA* 82, 4592–4596 [1985]).

The term "variable" refers to the fact that certain portions of the variable domains differ extensively in sequence among antibodies and are used in the binding and specificity of each particular antibody for its particular antigen. However, the variability is not evenly distributed through the variable domains of antibodies. It is concentrated in three segments called complementarity determining regions (CDRs) or hypervariable regions both in the light chain and the heavy chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat, E. A. et al., *Sequences of Proteins of Immunological Interest*, National Institute of Health, Bethesda, Md. [1991]). The constant domains are not involved directly in binding an antibody to an antigen, but exhibit various effector functions, such as participation of the antibody in antibody-dependent cellular toxicity.

Papain digestion of antibodies produces two identical antigen binding fragments, called Fab fragments, each with a single antigen binding site, and a residual "Fc" fragment, whose name reflects its ability to crystallize readily. Pepsin treatment yields an F(ab')$_2$ fragment that has two antigen combining sites and is still capable of cross-linking antigen.

"Fv" is the minimum antibody fragment which contains a complete antigen recognition and binding site. This region consists of a dimer of one heavy and one light chain variable domain in tight, non-covalent association. It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab)$_2$ antibody fragments originally were produced as pairs of Fab' fragments which have hinge cysteines between them. Other, chemical couplings of antibody fragments are also known.

The light chains of antibodies (immunoglobulins) from any vertebrate species can be assigned to one of two clearly distinct types, called kappa and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g. IgG-1, IgG-2, lgG-3, and IgG-4; IgA-1 and IgA-2. The heavy chain constant domains that correspond to the different classes of immunoglobulins are called α, delta, epsilon, γ, and μ, respectively. The subunit structures and three-dimensional configurations of different classes of immunoglobulins are well known.

The term "antibody" is used in the broadest sense and specifically covers single monoclonal antibodies (including agonist and antagonist antibodies), antibody compositions with polyepitopic specificity, as well as antibody fragments (e.g., Fab, F(ab')$_2$, and Fv), so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler & Milstein, *Nature* 256:495 (1975), or may be made by recombinant DNA methods [see, e.g. U.S. Pat. No. 4,816,567 (Cabilly et al.)].

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567 (Cabilly et al.; Morrison et al., *Proc. Natl. Acad. Sci. USA* 81, 6851–6855 [1984]).

"Humanized" forms of non-human (e.g. murine) antibodies are chimeric immunoglobulins, immunoglobulin chains or fragments thereof(such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details see: Jones et al., *Nature* 321, 522–525 [1986]; Reichmann et al., *Nature* 332, 323–329 [1988]; EP-B-239 400 published Sep. 30, 1987; Presta, *Curr. Op. Struct. Biol.* 2 593–596 [1992]; and EP-B-451 216 published Jan. 24, 1996).

In the context of the present invention the expressions "cell", "cell line", and "cell culture" are used interchangeably, and all such designations include progeny. It is also understood that all progeny may not be precisely identical in DNA content, due to deliberate or inadvertent mutations. Mutant progeny that have the same function or biological property, as screened for in the originally transformed cell, are included.

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host cell. The vector is used to transport the foreign or heterologous DNA into a suitable host cell. Once in the host cell, the vector can replicate independently of the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

"Oligonucleotides" are short-length, single- or double-stranded polydeoxynucleotides that are chemically synthesized by known methods [such as phosphotriester, phosphite, or phosphoramidite chemistry, using solid phase techniques such as those described in EP 266,032, published May. 4, 1988, or via deoxynucleoside H-phosphanate intermediates as described by Froehler et al., *Nucl. Acids Res.* 14, 5399 (1986). They are then purified on polyacrylamide gels.

B. Production of PTP HSCs by recombinant DNA technology

1. Identification and isolation of nucleic acid encoding PTP HSCs

The native PTP HSC proteins of the present invention may be isolated from relatively undifferentiated, early hematopoietic stem or progenitor cells. The isolation of murine PTP HSC from the CD34$^{hi}$ fraction of murine 10.5 day yolk sac or embryo cells is illustrated in the examples. Similarly, murine PTP HSC can be isolated from CD34$^{hi}$ population originated from bone marrow or fetal liver. The purity of these murine cells was found to be a critical step in isolating the mRNA encoding the new murine PTP HSC of the present invention. A high degree of purity was achieved by purification with a rabbit anti-murine CD34 antibody followed by a lineage depletion step and a positive selection step with the Sca antibody. Alternatively, murine PTP HSC can be detected and obtained from other relatively undifferentiated precursors of mature murine hematopoietic cells, such as, BAF 3, 32D and FDCP hematopoietic progenitor cells, available from the American Type Culture Collection (ATCC). Native human PTP HSC can, for example, be identified in and obtained from human CMK progenitor cells. As the PTP HSCs enzymes have an extremely low abundance in embryonic tissues, their purification by traditional methods would be very cumbersome and inefficient. Instead, cDNA or genomic clones encoding the PTP HSC proteins of the present invention can be prepared using standard techniques of recombinant DNA technology. For example, cDNA library can be constructed by obtaining polyadenylated mRNA from a cell line known to express the desired PTP HSC, and using the mRNA as a template to synthesize double stranded cDNA. Exemplary human and non-human cell lines suitable for this purpose have been listed hereinabove. A PTP HSC polypeptide gene can also be obtained from a genomic library, such as a human genomic cosmid library.

Libraries, either cDNA or genomic, are then screened with probes designed to identify the gene of interest or the protein encoded by it. For cDNA expression libraries, suitable probes include monoclonal and polyclonal antibodies that recognize and specifically bind to a PTP HSC polypeptide. For cDNA libraries, suitable probes include carefully selected oligonucleotide probes (usually of about 20–80 bases in length) that encode known or suspected portions of a PTP HSC polypeptide from the same or different species, and/or complementary or homologous cDNAs or fragments thereof that encode the same or a similar gene. Appropriate probes for screening genomic DNA libraries include, without limitation, oligonucleotides, cDNAs, or fragments thereof that encode the same or a similar gene, and/or homologous genomic DNAs or fragments thereof. Screening the cDNA or genomic library with the selected probe may be conducted using standard procedures as described in Chapters 10–12 of Sambrook et al., *Molecular Cloning: A Laboratory Manual* New York, Cold Spring Harbor Laboratory Press, 1989.

If DNA encoding an enzyme of the present invention is isolated by using carefully selected oligonucleotide sequences to screen cDNA libraries from various tissues, the oligonucleotide sequences selected as probes should be sufficient in length and sufficiently unambiguous that false positives are minimized. The actual nucleotide sequence(s) is/are usually designed based on regions which have the least codon redundance. The oligonucleotides may be degenerate at one or more positions. The use of degenerate oligonucleotides is of particular importance where a library is screened from a species in which preferential codon usage is not known.

The oligonucleotide must be labeled such that it can be detected upon hybridization to DNA in the library being screened. The preferred method of labeling is to use ATP (e.g., $\gamma^{32}P$) and polynucleotide kinase to radiolabel the 5' end of the oligonucleotide. However, other methods may be used to label the oligonucleotide, including, but not limited to, biotinylation or enzyme labeling.

cDNAs encoding PTP HSCs can also be identified and isolated by other known techniques of recombinant DNA technology, such as by direct expression cloning, or by using the polymerase chain reaction (PCR) as described in U.S. Pat. No. 4,683,195, issued Jul. 28, 1987, in section 14 of Sambrook et al., supra, or in Chapter 15 of *Current Protocols in Molecular Biology*, Ausubel et al. eds., Greene Publishing Associates and Wiley-Interscience 1991. The use of the PCR technique for obtaining cDNA encoding murine PTP HSC or the PTP domain of this native protein is also illustrated in the examples.

Once cDNA encoding a PTP HSC enzyme from one species has been isolated, cDNAs from other species can also be obtained by cross-species hybridization. According to this approach, human or other mammalian cDNA or genomic libraries are probed by labeled oligonucleotide sequences selected from known PTP HSC sequences (such as murine PTP HSC) in accord with known criteria, among which is that the sequence should be sufficient in length and sufficiently unambiguous that false positives are minimized. Typically, a $^{32}$P-labeled oligonucleotide having about 30 to 50 bases is sufficient, particularly if the oligonucleotide contains one or more codons for methionine or tryptophan. Isolated nucleic acid will be DNA that is identified and separated from contaminant nucleic acid encoding other polypeptides from the source of nucleic acid. Hybridization is preferably performed under "stringent conditions" which means (1) employing low ionic strength and high temperature for washing, for example,0.015 sodium chloride/ 0.0015M sodium citrate/0.1% sodium dodecyl sulfate at 50° C., or (2) employing during hybridization a denaturing agent, such as formamide, for example, 50% (vol/vol) formamide with 0.1% bovine serum albumin/0.1% polyvinylpyrrolidone/50 nM sodium phosphate buffer at pH 6.5 with 650 mM sodium chloride, 75 mM sodium citrate at 42° C. Another example is the use of 50% formamide, 5×SSC (0.75 M sodium chloride, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS.

Once the sequence is known, the gene encoding a particular PTP HSC polypeptide can also be obtained by chemical synthesis, following one of the methods described in Engels and Uhlmann, *Agnew. Chem. Int. Ed. Engl.* 28, 716 (1989). These methods include triester, phosphite, phosphoramidite and H-phosphonate methods, PCR and other autoprimer methods, and oligonucleotide syntheses on solid supports.

2. Cloning and expression of nucleic acid encoding PTP HSCs

Once the nucleic acid encoding PTP HSC is available, it is generally ligated into a replicable expression vector for further cloning (amplification of the DNA), or for expression.

Expression and cloning vectors are well known in the art and contain a nucleic acid sequence that enables the vector to replicate in one or more selected host cells. The selection of the appropriate vector will depend on 1) whether it is to be used for DNA amplification or for DNA expression, 2) the size of the DNA to be inserted into the vector, and 3) the host cell to be transformed with the vector. Each vector contains various components depending on its function (amplification of DNA of expression of DNA) and the host cell for which it is compatible. The vector components generally include, but are not limited to, one or more of the following: a signal sequence, an origin of replication, one or more marker genes, an enhancer element, a promoter, and a transcription termination sequence. Construction of suitable vectors containing one or more of the above listed components, the desired coding and control sequences, employs standard ligation techniques. Isolated plasmids or DNA fragments are cleaved, tailored, and religated in the form desired to generate the plasmids required. For analysis to confirm correct sequences in plasmids constructed, the ligation mixtures are commonly used to transform *E. coli* cells, e.g. *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.* 9, 309 (1981) or by the method of Maxam et al., *Methods in Enzymology* 65, 499 (1980).

The polypeptides of the present invention may be expressed in a variety of prokaryotic and eukaryotic host cells. Suitable prokaryotes include gram negative or gram positive organisms, for example *E. coli* or bacilli. A preferred cloning host is *E. coli* 294 (ATCC 31,446) although other gram negative or gram positive prokaryotes such as *E. coli* B, *E. coli* X1776 (ATCC 31,537), *E. coli* W3110 (ATCC 27,325), Pseudomonas species, or *Serratia Marcesans* are suitable.

In addition to prokaryotes, eukaryotic microbes such as filamentous fungi or yeast are suitable hosts for vectors herein. *Saccharomyces cerevisiae*, or common baker's yeast, is the most commonly used among lower eukaryotic host microorganisms. However, a number of other genera, species and strains are commonly available and useful herein, such as *S. pombe* [Beach and Nurse, *Nature* 290, 140 (1981)], *Kluyveromyces lactis* [Louvencourt et al., *J. Bacteriol.* 737 (1983)]; *yarrowia* (EP 402,226); *Pichia pastoris* (EP 183,070), *Trichodermareesia* (EP 244,234), *Neurospora crassa* [Case et al., *Proc. Natl. Acad. Sci. USA* 76, 5259–5263 (1979)]; and Aspergillus hosts such as *A. nidulans* [Ballance et al., *Biochem. Biophys. Res. Commun.* 112, 284–289 (1983); Tilburn et al., *Gene* 26, 205–221 (1983); Yelton et al., *Proc. Natl. Acad. Sci. USA* 81, 1470–1474 (1984)] and *A. niger* [Kelly and Hynes, *EMBO J.* 4, 475–479 (1985)].

Suitable host cells may also derive from multicellular organisms. Such host cells are capable of complex processing and glycosylation activities. In principle, any higher eukaryotic cell culture is workable, whether from vertebrate or invertebrate culture, although cells from mammals such as humans are preferred. Examples of invertebrate cells include plants and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melangaster* (fruitfly), and *Bombyx mori* host cells have been identified. See, e.g. Luckow et al., *Bio/Technolgy* 6, 47–55 (1988); Miller et al., in *Genetic Engineering,* Setlow, J. K. et al., eds., Vol. 8 (Plenum Publishing, 1986), pp. 277–279; and Maeda et al., *Nature* 315, 592–594 (1985). A variety of such viral strains are publicly available, e.g. the L-1 variant of *Autographa californica* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens,* which has been previously manipulated to contain the PTP HSC DNA. During incubation of the plant cell culture with *A. tumefaciens,* the DNA encoding a PTP HSC is transferred to the plant cell host such that it is transfected, and will, under appropriate conditions, express the PTP HSC DNA. In addition, regulatory and signal sequences compatible with plant cells are available, such as the nopaline synthase promoter and polyadenylation signal sequences. Depicker et al., *J. Mol. Appl. Gen.* 1, 561 (1982). In addition, DNA segments isolated from the upstream region of the T-DNA 780 gene are capable of activating or increasing transcription levels of plant-expressible genes in recombinant DNA-containing plant tissue. See EP 321,196 published Jun. 21, 1989.

However, interest has been greatest in vertebrate cells, and propagation of vertebrate cells in culture (tissue culture) is per se well known. See *Tissue Culture,* Academic Press, Kruse and Patterson, editors (1973). Examples of useful mammalian host cell lines are monkey kidney CV1 line transformed by SV40 (COS-7, ATCC CRL 1651); human embryonic kidney cell line [293 or 293 cells subcloned for growth in suspension culture, Graham et al., *J. Gen. Virol.* 36, 59 (1977)]; baby hamster kidney cells 9BHK, ATCC CCL 10); Chinese hamster ovary cells/-DHFR [CHO, Urlaub and Chasin, *Proc. Natl. Acad. Sci. USA* 77, 4216 (1980)]; mouse sertolli cells [TM4, Mather, *Biol. Reprod.* 23, 243–251 (1980)]; monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL75); human liver cells (Hep G2, HB 8065); mouse mammary tumor (MMT 060562, ATCC CCL51); TRI cells [Mather et al., *Annals N.Y. Acad. Sci.* 383, 44068 (1982)]; MRC 5 cells; FS4 cells; and a human hepatoma cell line (Hep G2). Preferred host cells are human embryonic kidney 293 and Chinese hamster ovary cells.

Particularly useful in the practice of this invention are expression vectors that provide for the transient expression in mammalian cells of DNA encoding a PTP HSC. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient systems, comprising a suitable expression vector and a host cell, allow for the convenient positive identification of polypeptides encoded by clones DNAs, as well as for the rapid screening of such polypeptides for desired biological or physiological properties. Thus, transient expression systems are particularly useful in the invention for purposes of identifying analogs and variants of a PTP HSC. Other methods, vectors, and host cells suitable for adaptation to the synthesis of the PTP HSC polypeptides in recombinant vertebrate cell culture are described in Getting et al., *Nature* 293, 620–625 (1981); Mantel et al., *Nature* 281, 40–46 (1979); Levinson et al.; EP 117,060 and EP 117,058. Particularly useful plasmids for mammalian cell culture expression of the PTP HSC polypeptides are pRK5 (EP 307,247), or pSVI6B (PCT Publication No. WO 91/08291).

Other cloning and expression vectors suitable for the expression of the PTP HSCs of the present invention in a variety of host cells are, for example, described in EP 457,758 published Nov. 27, 1991. A large variety of expression vectors is now commercially available. An exemplary commercial yeast expression vector is pPIC.9 (Invitrogen), while an commercially available expression vector suitable for transformation of *E. coli* cells is PET15b (Novagen).

C. Culturing the Host Cells

Prokaryotes cells used to produced the PTP HSCs of this invention are cultured in suitable media as describe generally in Sambrook et al., supra.

Mammalian cells can be cultured in a variety of media. Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing the host cells. In addition, any of the media described in Ham and Wallace, *Meth. Enzymol.* 58, 44 (1979); Barnes and Sato, *Anal. Biochem.* 102, 255 (1980), U.S. Pat. Nos. 4,767,704; 4,657,866; 4,927,762; or 4,560,655; WO 90/03430; WO 87/00195 or U.S. Pat. No. Re.30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug) trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH and the like, suitably are those previously used with the host cell selected for cloning or expression, as the case may be, and will be apparent to the ordinary artisan.

The host cells referred to in this disclosure encompass cells in in vitro cell culture as well as cells that are within a host animal or plant.

It is further envisioned that the PTP HSCs of this invention may be produced by homologous recombination, or with recombinant production methods utilizing control elements introduced into cells already containing DNA encoding the particular PTP HSC.

D. Detecting Gene Amplification/Expression

Gene amplification and/or expression may be measured in a sample directly, for example, by conventional Southern blotting, Northern blotting to quantitate the transcription of mRNA Thomas, *Proc. Natl. Acad. Sci. USA* 77, 5201–5205 (1980)], dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as a site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to the surface, so that upon the formation of duplex on the surface, the presence of antibody bound to the duplex can be detected. Gene expression, alternatively, may be measured by immunological methods, such as immunohisto chemical staining of tissue sections and assay of cell culture or body fluids, to quantitate directly the expression of gene product. With immunohisto chemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hse et al., *Am. J. Clin. Pharm.* 75, 734–738 (1980).

Antibodies useful for immunohistochemical staining and/ or assay of sample fluids may be either monoclonal or polyclonal, and may be prepared in any animal. Conveniently, the antibodies may be prepared against a native PTP HSC polypeptide, or against a synthetic peptide based on the DNA sequence provided herein as described further hereinbelow.

E. Amino Acid Sequence Variants of a native PTP HSCs

Amino acid sequence variants of native PTP HSCs are prepared by methods known in the art by introducing appropriate nucleotide changes into a PTP HSC DNA, or by in vitro synthesis of the desired polypeptide. There are two principal variables in the construction of amino acid sequence variants: the location of the mutation site and the nature of the mutation. With the exception of naturally-occurring alleles, which do not require the manipulation of the DNA sequence encoding the PTP HSC, the amino acid sequence variants of PTP HSCs are preferably constructed by mutating the DNA, either to arrive at an allele or an amino acid sequence variant that does not occur in nature.

One group of the mutations will be created within the phosphatase (PTP) domain of the enzymes of the present invention. Non-conservative substitutions within this domain may result in PTP HSC variants which loose their ability to dephosphatase tyrosines and will, therefore, be useful as antagonists of native PTP HSCs. PTP HSC variants mutated to enhance their enzymatic activity will be useful, for example, as more effective inhibitors of progenitor/stem cell differentiation.

Alternatively or in addition, amino acid alterations can be made at sites that differ in PTP HSC proteins from various species, or in highly conserved regions, depending on the goal to be achieved. Sites at such locations will typically be modified in series, e.g. by (1) substituting first with conservative choices and then with more radical selections depending upon the results achieved, (2) deleting the target residue or residues, or (3) inserting residues of the same or different class adjacent to the located site, or combinations of options 1–3. One helpful technique is called "alanine scanning" (Cunningham and Wells, *Science* 244, 1081–1085 [1989]).

After identifying the desired mutation(s), the gene encoding a PTP HSC variant can, for example, be obtained by chemical synthesis as hereinabove described. More preferably, DNA encoding a PTP HSC amino acid sequence variant is prepared by site-directed mutagenesis of DNA that encodes an earlier prepared variant or a nonvariant version of the PTP HSC. Site-directed (site-specific) mutagenesis allows the production of PTP HSC variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the techniques of site-specific mutagenesis are well known in the art, as exemplified by publications such as, Edelman et al., *DNA* 2, 183 (1983). As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA* A. Walton, ed., Elsevier, Amsterdam (1981). This and other phage vectors are commercially available and their use is well known to those skilled in the art. A versatile and efficient procedure for the construction of oligodeoxyribonucleotidedirected site-specific mutations in DNA fragments using M13-derived vectors was published by Zoller, M. J. and Smith, M., *Nucleic Acids Res.* 10, 6487–6500 [1982]). Also, plasmid vectors that contain a single-stranded phage origin of replication (Veira et al., *Meth. Enzymol.* 3 [1987]) may be employed to obtain single-stranded DNA. Alternatively, nucleotide substitutions are introduced by synthesizing the appropriate DNA fragment in vitro, and amplifying it by PCR procedures known in the art.

The PCR technique may also be used in creating amino acid sequence variants of a PTP HSC. In a specific example of PCR mutagenesis, template plasmid DNA (1 µg) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphates and is included in the GeneAmp® kits (obtained from Perkin-Elmer Cetus, Norwalk, Conn. and Emeryville, Calif.), and 25 pmole of each oligonucleotide primer, to a final volume of 50 µl. The reaction mixture is overlayered with 35 µl mineral oil. The reaction is denatured for 5 minutes at 100° C., placed briefly on ice, and then 1 µl *Thermus aquaticus* (Taq) DNA polymerase (5 units/l), purchased from Perkin-Elmer Cetus, Norwalk, Conn. and Emeryville, Calif.) is added below the mineral oil layer. The reaction mixture is then inserted into a DNA Thermal Cycler (purchased from Perkin-Elmer Cetus) programmed as follows:

2 min. 55° C.,
30 sec. 72° C., then 19 cycles of the following:
30 sec. 94° C.,
30 sec. 55° C., and
30 sec. 72° C.

At the end of the program, the reaction vial is removed from the thermal cycler and the aqueous phase transferred to a new vial, extracted with phenol/chloroform (50:50 vol), and ethanol precipitated, and the DNA is recovered by standard procedures. This material is subsequently subjected to appropriate treatments for insertion into a vector.

Another method for preparing variants, cassette mutagenesis, is based on the technique described by Wells et al. [*Gene* 34, 315 (1985)].

Additionally, the so-called phagemid display method may be useful in making amino acid sequence variants of native or variant PTP HSCs or their fragments. This method involves (a) constructing a replicable expression vector comprising a first gene encoding an receptor to be mutated, a second gene encoding at least a portion of a natural or wild-type phage coat protein wherein the first and second genes are heterologous, and a transcription regulatory element operably linked to the first and second genes, thereby forming a gene fusion encoding a fusion protein; (b) mutating the vector at one or more selected positions within the first gene thereby forming a family of related plasmids; (c) transforming suitable host cells with the plasmids; (d) infecting the transformed host cells with a helper phage having a gene encoding the phage coat protein; (e) culturing the transformed infected host cells under conditions suitable for forming recombinant phagemid particles containing at least a portion of the plasmid and capable of transforming the host, the conditions adjusted so that no more than a minor amount of phagemid particles display more than one copy of the fusion protein on the surface of the particle; (f) contacting the phagemid particles with a suitable antigen so that at least a portion of the phagemid particles bind to the antigen; and (g) separating the phagemid particles that bind from those that do not. Steps (d) through (g) can be repeated one or more times. Preferably in this method the plasmid is under tight control of the transcription regulatory element, and the culturing conditions are adjusted so that the amount or number of phagemid particles displaying more than one copy of the fusion protein on the surface of the particle is less than about 1%. Also, preferably, the amount of phagemid particles displaying more than one copy of the fusion protein is less than 10% of the amount of phagemid particles displaying a single copy of the fusion protein. Most preferably, the amount is less than 20%. Typically in this method, the expression vector will further contain a secretory signal sequence fused to the DNA encoding each subunit of the polypeptide and the transcription regulatory element will be a promoter system. Preferred promoter systems are selected from lac Z, $\lambda_{PL}$, tac, T7 polymerase, tryptophan, and alkaline phosphatase promoters and combinations thereof. Also, normally the method will employ a helper phage selected from M13K07, M13R408, M13-VCS, and Phi X 174. The preferred helper phage is M13K07, and the preferred coat protein is the M13 Phage gene III coat protein. The preferred host is *E. coli*, and protease-deficient strains of *E. coli*.

Further details of the foregoing and similar mutagenesis techniques are found in general textbooks, such as, for example, Sambrook et al., supra, and *Current Protocols in Molecular Biology,* Ausubel et al. eds., supra.

Naturally-occurring amino acids are divided into groups based on common side chain properties:
(1) hydrophobic: norleucine, met, ala, val, leu, ile;
(2) neutral hydrophobic: cys, ser, thr;
(3) acidic: asp, glu;
(4) basic: asn, gin, his, lys, arg;
(5) residues that influence chain orientation: gly, pro; and
(6) aromatic: trp, tyr, phe.

Conservative substitutions involve exchanging a member within one group for another member within the same group, whereas non-conservative substitutions will entail exchanging a member of one of these classes for another.

Amino acid sequence deletions generally range from about 1 to 30 residues, more preferably about 1 to 10 residues, and typically are contiguous.

Amino acid insertions include amino- and/or carboxyl-terminal fusions ranging in length from one residue to polypeptides containing a hundred or more residues, as well as intrasequence insertions of single or multiple amino acid residues. Intrasequence insertions (i.e. insertions within the PTP HSC protein amino acid sequence) may range generally from about 1 to 10 residues, more preferably 1 to 5 residues, more preferably 1 to 3 residues. Examples of terminal insertions include the PTP HSC polypeptides with an N-terminal methionyl residue, an artifact of its direct expression in bacterial recombinant cell culture, and fusion of a heterologous N-terminal signal sequence to the N-terminus of the PTP HSC molecule to facilitate the secretion of the mature PTP HSC from recombinant host cells. Such signal sequences will generally be obtained from, and thus homologous to, the intended host cell species. Suitable sequences include STII or Ipp for *E. coli,* alpha factor for yeast, and viral signals such as herpes gD for mammalian cells.

Other insertional variants of the native PTP HSC molecules include the fusion of the N- or C-terminus of the TRAF molecule to immunogenic polypeptides, e.g. bacterial polypeptides such as beta-lactamase or an enzyme encoded by the *E. coli* trp locus, or yeast protein, and C-terminal fusions with proteins having a long half-life such as immunoglobulin regions (preferably immunoglobulin constant regions), albumin, or ferritin, as described in WO 89/02922 published on Apr. 6, 1989.

Since it is often difficult to predict in advance the characteristics of a variant PTP HSC, it will be appreciated that some screening will be needed to select the optimum variant.

F. Covalent Modifications of PTP HSC Polypeptides

Covalent modifications of PTP HSCs are included within the scope herein. Such modifications are traditionally introduced by reacting targeted amino acid residues of the PTP HSC polypeptides with an organic derivatizing agent that is capable of reacting with selected sides or terminal residues, or by harnessing mechanisms of post-translational modifications that function in selected recombinant host cells. The resultant covalent derivatives are useful in programs directed at identifying residues important for biological activity, for immunoassays of the PTP HSC, or for the preparation of anti-PTP HSC antibodies for inmmunoaffinity purification of the recombinant. For example, complete inactivation of the biological activity of the protein after reaction with ninhydrin would suggest that at least one arginyl or lysyl residue is critical for its activity, whereafter the individual residues which were modified under the conditions selected are identified by isolation of a peptide fragment containing the modified amino acid residue. Such modifications are within the ordinary skill in the art and are performed without undue experimentation.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyldisulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay.

Carboxyl side groups (aspartyl or glutamyl) are selectively modified by reaction with carbodiimides (R'—N=C=N—R') such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl, threonyl or tyrosyl residues, methylation of the α-amino groups of lysine, arginine, and histidine side chains (T. E. Creighton, *Proteins: Structure and Molecular Properties,* W. H. Freeman & Co., San Francisco, pp. 79–86 [1983]), acetylation of the N-terminal amine, and amidation of any C-terminal carboxyl group. The molecules may further be covalently linked to nonproteinaceous polymers, e.g. polyethylene glycol, polypropylene glycol or polyoxyalkylenes, in the manner set forth in U.S. Ser. No. 07/275,296 or U.S. Pat. Nos. 4,640,835; 4,496,689; 4,301,144; 4,670,417; 4,791,192 or 4,179,337.

Derivatization with bifunctional agents is useful for preparing intramolecular aggregates of the PTP HSCs with polypeptides as well as for cross-linking the PTP HSC polypeptide to a water insoluble support matrix or surface for use in assays or affinity purification. In addition, a study of interchain cross-links will provide direct information on conformational structure. Commonly used cross-linking agents include 1,1-bis(diazoacetyl)-2-phenylethane, glutaraldehyde, N-hydroxysuccininide esters, homobifunctional imidoesters, and bifunctional maleimides. Derivatizing agents such as methyl-3-[(p-azidophenyl)dithio] propioimidate yield photoactivatable intermediates which are capable of forming cross-links in the presence of light. Alternatively, reactive water insoluble matrices such as cyanogen bromide activated carbohydrates and the systems reactive substrates described in U.S. Pat. Nos. 3,959,642; 3,969,287; 3,691,016; 4,195,128; 4,247,642; 4,229,537; 4,055,635; and 4,330,440 are employed for protein immobilization and cross-linking.

Certain post-translational modifications are the result of the action of recombinant host cells on the expressed polypeptide. Glutaminyl and aspariginyl residues are frequently post-translationally deamidated to the corresponding glutamyl and aspartyl residues. Alternatively, these residues are deamidated under mildly acidic conditions. Either form of these residues falls within the scope of this invention.

Other post-translational modifications include hydroxylation of proline and lysine, phosphorylation of hydroxyl groups of seryl, threonyl or tyrosyl residues, methylation of the α-amino groups of lysine, arginine, and histidine side chains [T. E. Creighton, *Proteins: Structure and Molecular Properties*, W. H. Freeman & Co., San Francisco, pp. 79–86 (1983)].

Other derivatives comprise the novel peptides of this invention covalently bonded to a nonproteinaceous polymer. The nonproteinaceous polymer ordinarily is a hydrophilic synthetic polymer, i.e. a polymer not otherwise found in nature. However, polymers which exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. Particularly useful are polyvinylalkylene ethers such a polyethylene glycol, polypropylene glycol.

The PTP HSC polypeptides may be linked to various nonproteinaceous polymers, such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337.

The PTP HSCs may be entrapped in microcapsules prepared, for example, by coacervation techniques or by interfacial polymerization, in colloidal drug delivery systems (e.g. liposomes, albumin microspheres, microemulsions, nano-particles and nanocapsules), or in macroemulsions. Such techniques are disclosed in *Remington's Pharmaceutical Sciences*, 16th Edition, Osol, A., Ed. (1980).

G. Anti-PTP HSC antibody preparation (i) Polyclonal antibodies

Polyclonal antibodies to a PTP HSC molecule generally are raised in animals by multiple subcutaneous (sc) or intraperitoneal (ip) injections of the PTP HSC and an adjuvant. It may be useful to conjugate the PTP HSC or a fragment containing the target amino acid sequence to a protein that is immunogenic in the species to be immunized, e.g. keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glytaraldehyde, succinic anhydride, $SOCl_2$, or $R^1N=C=NR$, where R and $R^1$ are different alkyl groups.

Animals are immunized against the immunogenic conjugates or derivatives by combining 1 mg or 1 μg of conjugate (for rabbits or mice, respectively) with 3 volumes of Freud's complete adjuvant and injecting the solution intradermally at multiple sites. One month later the animals are boosted with ⅕ to ¹/₁₀ the original amount of conjugate in Freud's complete adjuvant by subcutaneous injection at multiple sites. 7 to 14 days later the animals are bled and the serum is assayed for anti-PTP HSC antibody titer. Animals are boosted until the titer plateaus. Preferably, the animal boosted with the conjugate of the same PTP HSC, but conjugated to a different protein and/or through a different cross-linking reagent. Conjugates also can be made in recombinant cell culture as protein fusions. Also, aggregating agents such as alum are used to enhance the immune response.

(ii) Monoclonal antibodies

Monoclonal antibodies are obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies.

For example, the anti-PTP HSC monoclonal antibodies of the invention may be made using the hybridoma method first described by Kohler & Milstein, Nature 256:495 (1975), or may be made by recombinant DNA methods [Cabilly, et al., U.S. Pat. No. 4,816,567].

In the hybridoma method, a mouse or other appropriate host animal, such as hamster is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell [Goding, *Monoclonal Antibodies: Principles and Practice*, pp.59–103 (Academic Press, 1986)].

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high level expression of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies [Kozbor, J. Immunol. 133:3001 (1984); Brodeur, et al., *Monoclonal Antibody Production Techniques and Applications,* pp.51–63 (Marcel Dekker, Inc., New York, 1987)].

Culture medium in which hybridoma cells are growing is assayed for production of monoclonal antibodies directed against PTP HSC. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson & Pollard, Anal. Biochem. 107:220 (1980).

After hybridoma cells are identified that produce antibodies of the desired specificity, affinity, and/or activity, the clones may be subcloned by limiting dilution procedures and grown by standard methods. Goding, *Monoclonal Antibodies: Principles and Practice,* pp.59–104 (Academic Press, 1986). Suitable culture media for this purpose include, for example, Dulbecco's Modified Eagle's Medium or RPMI-1640medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison, el al., *Proc. Nat. Acad. Sci.* 81, 6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-TRAF monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for a PTP HSC and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

For diagnostic applications, the antibodies of the invention typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; biotin; radioactive isotopic labels, such as, e.g., $^{125}I$, $^{32}P$, $^{14}C$, or $^3H$, or an enzyme, such as alkaline phosphatase, beta-galactosidase or horseradish peroxidase.

Any method known in the art for separately conjugating the antibody to the detectable moiety may be employed, including those methods described by Hunter, et al., *Nature* 144:945 (1962); David, et al., *Biochemistry* 13:1014 (1974); Pain, et al., *J. Immunol. Meth.* 40:219 (1981); and Nygren, *J. Histochem. and Cytochem.* 30:407 (1982).

The antibodies of the present invention may be employed in any known assay method, such as competitive binding assays, direct and indirect sandwich assays, and immunoprecipitation assays. Zola, *Monoclonal Antibodies: A Manual of Techniques,* pp.147–158 (CRC Press, Inc., 1987).

Competitive binding assays rely on the ability of a labeled standard (which may be a PTP HSC polypeptide or an immunologically reactive portion thereof) to compete with the test sample analyte (PTP HSC) for binding with a limited amount of antibody. The amount of PTP HSC in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex. David & Greene, U.S. Pat No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

(iii) Humanized antibodies

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature* 321, 522–525 (1986); Riechmann et al., *Nature* 332, 323–327 (1988); Verhoeyen et al., *Science* 239, 1534–1536 (1988)], by substituting rodent CDRs or CDR sequences for the corresponding sequences of a human antibody. Accordingly, such "humanized" antibodies are chimeric antibodies (Cabilly, supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details see U.S. application Ser. No. 07/934,373 filed Aug. 21, 1992, which is a continuation-in-part of application Ser. No. 07/715,272 filed Jun. 14, 1991.

Alternatively, it is now possible to produce transgenic animals (e.g. mice) that are capable, upon immunization, of producing a full repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., *Proc. Natl. Acad. Sci. USA* 90, 2551–255 (1993); Jakobovits et al., *Nature* 362, 255–258 (1993).

(iv) Bispecific antibodies

Bispecific antibodies are monoclonal, preferably human or humanized, antibodies that have binding specificities for at least two different antigens. In the present case, one of the binding specificities is for a PTP HSC, the other one is for any other antigen, for example an antigen expressed on the surface of a leukemia cell, if the antibody is an antagonist of a native PTP HSC and is used to induce differentiation of undifferentiated lekemia cells. If an agonist antibody specifically binding to a native PTP HSC is used to expand stem cells with growth factors, as hereinafter described, the second specificity could be provided by a stem cell growth factor. Such constructs can also be referred to as bispecific immunoadhesins. Methods for making bispecific antibodies (and bispecific immunoadhesins) are known in the art.

Traditionally, the recombinant production of bispecific antibodies is based on the coexpression of two immunoglobulin heavy chain-light chain pairs, where the two heavy chains have different specificities (Millstein and Cuello, *Nature* 305, 537–539 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT application publication No. WO 93/08829 (published May 13, 1993), and in Traunecker et al., *EMBO* 10, 3655–3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, and second and third constant regions of an immunoglobulin heavy chain (CH2 and CH3). It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in copending application Ser. No. 07/931,811 filed Aug. 17, 1992.

For further details of generating bispecific antibodies see, for example, Suresh et al., *Methods in Enzymology,* 121, 210 (1986).

(v) Heteroconjugate antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (PCT application publication Nos. WO 91/00360 and WO 92/200373;EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

H. Peptide and non-peptide analogs of polypeptide PTP HSCs

Peptide analogs of the PTP HSC polypeptides of the present invention are modelled based upon the three-dimensional structure of the native polypeptides. Peptides may be synthesized by well known techniques such as the solid-phase synthetic techniques initially described in Merrifield, *J. Am. Chem. Soc.* 15, 2149–2154 (1963). Other peptide synthesis techniques are, for examples, described in Bodanszky et al., Peptide Synthesis, John Wiley & Sons, 2nd Ed., 1976, as well as in other reference books readily available for those skilled in the art. A summary of peptide synthesis techniques may be found in Stuart and Young, Solid Phase Peptide Synthelia, Pierce Chemical Company, Rockford, Ill. (1984). Peptides may also be prepared by recombinant DNA technology, using a DNA sequence encoding the desired peptide.

In addition to peptide analogs, the present invention also contemplates non-peptide (e.g. organic) compounds which display substantially the same surface as the peptide analogs of the present invention, and therefore interact with other molecules in a similar fashion.

I. Use of the PTP HSCs

The PTP HSCs of the present invention are useful for a variety of purposes. For example, native PTP HSCs are useful for the identification and isolation of a PTP HSC analog in another mammalian species. Native PTP HSCs and their functional equivalents are also useful in screening assays designed to identify agonist of antagonist of native PTP HSCs. Such assays may take the form of any conventional cell-type or biochemical binding assay, and can be performed in a variety of assay formats well known for those skilled in the art. As example is the so called "two-hybrid" assay format using the Matchmaker Two-Hybrid System (Clontech) according to the manufacturer's instructions.

The PTP HSCs of the present invention as well as their agonists can additionally be used for the maintenance of stem/progenitor cells in cell culture. Agonists which inhibit differentiation but allow for hematopoietic stem cell growth are particularly useful for this purpose, since their use results in an amplification of the stem cells without differentiation (self-renewal). This process might be useful, as an example, for the expansion of hematopoietic stem cells prior to autologous or heterologous bone marrow transplantation. The same approach can be used in vivo for the expansion of stem cells with growth factors, in the absence of diferentiation.

It is believed that the native PTP HSCs of the present invention may be expressed in leukemic cells. Accordingly, antagonist of the PTP HSCs of the present invention may be used for the induction of differentiation of undifferentiated leukemia cells. This might allow for aggressive undifferentiated leukemia cells to become differentiated, which, in turn, facilitates their treatment.

PTP HSC antagonists may also be used to induce differentiation of hematopoietic stem cells. As inhibition of the native PTP HSC enzyme might induce progenitor cells to differentiate, an antagonist of PTP HSC might act as a pan-inducer of myeloid, erythroid and lymphoid production. This use of PTP HSC antagonists may obviate or decrease the need for the use of stem cell growth factors.

Further details of the invention are illsutrated in the following non-limiting examples.

EXAMPLE 1

Identification and Cloning of Murine PTP HSC

A. Materials and Methods
Isolation of embryonic $lin^{lo}CD34^{hi}Sca^{hi}$ hematopoietic stem cells.

Yolk sacs or embryos were dissected from timed pregnant females at day 10.5. Fetal livers were isolated from day 13.5–14 embryos. Yolk sac and embryonic tissues were dissociated with 1% collagenase in RPMI medium at 37° C. for 15 minutes. Cells were further dissociated by two passages through a 16 gauge needle. Fetal liver was only dissociated by passage through a 16 guage needle. Adherent cells were attached to plastic by overnight incubation, after which the non adherent hematopoietic cells were incubated with a lineage cocktail of antibodies (1 μg each of TER 119, Gr-1, Ly-1, transferrin receptor and B220) for 1 hr on ice. Cells were washed, and the lineage positive cells were depleted using magnetic beads and a Miltenyi column. Lineage negative cells were pelleted, resuspended in 2% FCS, PBS and incubated with rabbit anti-murine CD34 antibody (Baumhueter et al., Science 262, 436–38 [1993]) on ice for 1 hr. Cells were washed three times in 2% FCS, PBS, resuspended in the same buffer and incubated with donkey, anti-rabbit FITC conjugated antibody and, in some cases, PE conjugated anti Sca antibody for 1 hr on ice. The cells were washed five times with 2% FCS, PBS, and than isolated by cell sorting on an ELITE cell sorter.

PCR analysis of mRNA isolated from $lin^{Lo}CD34^{hi}Sca^{hi}$ hematopoietic stem cells.

Messenger RNA was isolated from the $Lin^{Lo}CD34^{hi}Sca^{hi}$ fraction of fetal yolk-sac hematopoietic cells (MicroFastTrack,InVitrogene). Poly A+ RNA was reverse transcribed with random hexamers (Promega) and Moloney murine Leukemia virus revere transcriptase (SuperScript II, GIBCO BRL). ¼ of this cDNA was amplified by PCR using degenerate mixed oligonucleotides primers. Sense and antisense primers corresponding to the concensus PTP amino acid sequences $^H/_DFWRM^I/_VW$ (5'-$AC/_TTT^C/_TTGG^A/_C$ GIATG$^A/_G$TITGG-3') (SEQ. ID. NO: 14, where the degenerate positions are designated by "N") and $WPD^F/_HGVP$ (5'-GGIAC$^G/_A$$^T/_A$$^G/_A$$^G/_A$TCIGGCCA-3') (SEQ. ID. NO: 15, wherein the degenerate positions are designated by "N") respectively were used. PCR were carry out in 1×Taq DNA polymerase buffer (GIBCO BRL) plus 0.2 mM of each dNTP, 10% DMSO and 5 units Taq polymerase (GIBCO BRL) for 25 cycles of 94° C. for 1 minute, 55° C. for 1 min and 72° C. for 1 minute. The PCR products were treated with Klenow enzyme (New England Biolabs) at 30° C. for 30 minutes, cloned into SmaI site of pRK-5 (EP 307,247, published Mar. 15, 1989) plasmid, and subsequently sequenced (Sequenase, USB).
cDNA and genomic cloning.

Adapter-linked double strain cDNA was prepared from A+ RNA of day-10 murine embryos (Marathon-ready cDNA synthesize kit, Clontech) using either random hexamer or oligo dT primer. Full-length cDNA was isolated by 5' or 3' rapid amplification of cDNA ends (RACE) of the marathon-ready cDNAs. Genomic clones encoding the PTP HSC gene were isolated using standard techniques. The plaque purified lambda phage DNA was digested with Not 1, and the insert fragment was directly cloned without purification into Not 1 digested Bluescript. Exons were mapped using a combination of restriction digestion and southern blotting as well as DNA sequencing using custom primers.
Bacterial expression of the PTP.

cDNA sequences encode amino acid 8 to 323 containing the phosphatase domain were obtained by PCR using sense oligomer 5'-CACGGTCGACGGTGAGGAGCTTCTITG AGCAGCTGGAGG-3' (SEQ. ID. NO: 3), and antisense oligomer 5'-GTTGCGGCCGCGATTGGAGCGCAGTTC TCCTTGAGGTTCTGG-3' (SEQ. ID. NO: 4). The PCR fragment was treated with SalI and NotI restriction enzyme and cloned into SalI and NotI digested pGEX-4T-1 plasmid (Pharmacia). Fusion protein was affinity purified using a glutathione sepharose column (Pharmacia). Tyrosine phosphatase assays on the GST-fusion protein were carried out following the manufacture's procedure using two different tyrosine phosphorylated peptides from a tyrosine phosphatase assay kit (Boehringer Mannheim).

Quantitative PCR analysis of RNA isolated from hematopoietic cells.

cDNA was made from +RNA by reverse transcription (RT) with random hexamer. PCR was then used to amplified quantitatively PTP HSC cDNA and, as an internal standard, triosephosphate isomerase (TPI) cDNA. For each PCR, 6 ul of the 20 ul RT reaction was brought to 50 ul so as to contain 0.3 mM of dNTPs, 4 $\mu$Ci of $^{32}$P dATP (3,000 Ci/mmol, Amersham), 100 pmol of each of the four primers, and 5 units of Taq DNA polymerase (GIBCO BRL). Seventeen PCR cycles of 94° C. for 50 seconds, 55° C. for 50 seconds, and 70° C. for 70 seconds. One-tenth of each PCR samples was electrophoresed in a 6% polyacrylamide gel, and the PCR products were quantitate by phosphor imaging (Fuji). Conditions for accurate quantitation of either PTP HSC or TPI were assessed in experiments that used serial dilutions of a standard preparation of A+ RNA from 32D cells to determine for each primer pair the times of primer annealing and primer extension and the cycles that provided for a linear correlation between the amount of template RNA and the PCR product. Under the PCR conditions ultimately chosen, certain amount of sample RNA was analyzed simultaneously with serial dilutions of the standard RNA and a reverse transcriptase minus control.

Northern blot analysis of tissues and cell lines.

A SalI-NotI 1.3 kb PTP HSC cDNA fragment was used to probe murine multi-tissue northern blot (Clontech). The same northern blot was used with various other probes, all of which demonstrated detectable, undegraded transcripts.

PCR Primer Pairs

5'RACE primers: antisense primer 5'-CCTGGAGGGTCC TGAGAGTGATGTCTGCATTCAGTG-3' (SEQ. ID. NO: 5), 5'-CCTCTTGGAGCAGGGAAAGGATGACTC TTGTCTC-3' (SEQ. ID. NO: 6), 5'-CAGCTGCTCCAA GAAGCTCCTCACCAAGTC-3' (SEQ. ID. NO: 7). Sense primer: AP1 and AP2 (Clontech).

3'RACE primers: sense primer 5'-GGTAGAGGTGGG CAGGGTGAAGTGTTCTCGC-3' (SEQ. ID. NO: 8), 5'-CACTGAATGCAGACATCACTCTCAGGACCC TCCAGG-3' (SEQ. ID. NO: 9), 5'-GAGACAAGAGTC ATCCTTTCCCTG CTCCAAGAGG-3' (SEQ. ID. NO: 10). Antisense primer: AP1 and AP2 (Clontech).

Quantitative RT-PCR primers: PTP HSC sense primer 5'-CACTGAATGCAGACATCACTCTCAGGACCC TCCAGG-3' (SEQ. ID. NO: 9), antisense primer 5'-GAATGGTAACCTGGAGGGTCCTGAG-3' (SEQ. ID. NO: 11). TPI sense primer 5'-GAGAAGGTCGTG TTCGAG (SEQ. ID. NO: 12), antisense primer 5'-GTG TACTTCCTGTGCCTG-3' (SEQ. ID. NO: 13).

B. cDNA Cloning of PTPs from Hematopoietic Stem Cells

In order to analyze PTPs potentially involved with the maintenance of the hematopoietic stem cell, we isolated a highly purified population of these cells from either the murine 10.5 day yolk sac or embryo. Previously, we showed that both progenitor activity as well as stromal cell repopulating activity were found in the CD34$^{hi}$ fraction of these embryonic cells (C. Fennie and L. Lasky-unpublished observations). In addition, others have shown that the murine CD34$^{hi}$ population isolated from bone marrow (Krause et al., Blood 4(3), 691–701 [1994]), or fetal liver (Ziegler et al., Blood 84, 2422–2450 [1994]) contains stem cells capable of reconstituting lethally irradiated animals. In order to isolate a more highly purified fraction of these progenitor cells, we included a lineage depletion step as well as a positive selection step with the Sca antibody (Uchida et al., Blood 83(12), 3758–3779 [1994]), in addition to the CD34 antibody. These morphologically primitive hematopoietic cells show a higher degree of stromal cell repopulating ability as well as cobblestone formation as compared to the previously described CD34$^{hi}$ progenitor cells, and we are currently investigating their in vivo repopulating activity (C.Fennie and L. Lasky-unpublished observations). Previous investigators have shown that the lin$^{lo}$Sca$^{hi}$ fraction of bone marrow hematopoietic cells has a high level of repopulating activity (Sprangrude et al., Science A, 241, 58–62 [1988]). Thus, it is likely that the lin$^{lo}$CD34$^{hi}$Sca$^{hi}$ cells isolated from the early embryo contain self renewing hematopoietic stem cells (Uchida et al., supra; Krause et al., supra; Ziegler et al., supra).

Consensus PCR using primers derived from two highly conserved regions of the PTP phosphatase domain resulted in the cloning and sequencing of ~70 PCR fragments. A diversity of known receptor and non-receptor PTPs were detected in this fraction of these progenitor cells, and many of these PTPs have not previously been described in the hematopoietic stem cell compartment. Two novel PTPs were also isolated. One is a receptor PTP which is related to the homotypically interacting $\mu$, $\kappa$ and LAR family and is the subject of a patent application filed concurrently herewith. The second PTP was found to be most homologous to two previously described non-receptor PTPs, murine PTP PEP (Matthews et al., Mol. Cell Biol. 12(5), 2396–2405 [1992]) and murine/human PTP PEST (Takekawa et al., Biochem. Biophys. Res. Commun. 189(2),1223–1230 [1992]; Yang et al., J. Biol. Chem. 268(23) 17650 [1993]; and Charest et al., Biochem J. 308(2),425–432 [1995]), both of which contain a region that is very high in proline, glutamate, serine and threonine (the "PEST" domain). One of these PTPs, PEP, has been demonstrated to be localized to the nucleus (Flores et al., supra) (see below), so it appeared that the novel PTP fragment may have been a new member of this potentially nuclear-localized PTP family.

Initial PCR and northern analyses with the PTP fragment revealed that the transcript encoding this enzyme is extremely rare in embryonic and adult tissues. Thus, the fill length cDNA was cloned using the RACE procedure and RNA isolated from day 10 embryos. Because the RACE cloning of the 5 prime region was particularly difficult, the final 5 prime sequence was confirmed using the genomic clone encoding this PTP. As can be seen in FIG. 1, this transcript encodes an open reading frame of 453 amino acids specifying a protein of molecular weight 50,253 daltons. Homology searches revealed that the region encoding amino acids 25–290 were highly homologous to a variety of PTPs, with the highest degree of homology with murine PTP PEP (Matthews et al., supra) and murine/human PTP PEST (Takekawa et al., supra; Yang et al., supra; and Charest et al., supra) (FIG. 2). Interestingly, PTP PEP has also been found to be expressed in mature hematopoietic cells (Matthews et al., supra, Flores et al., supra) although human and murine PTP PEST appear to have a more generalized expression pattern (Yang et al., supra; Charest et al., supra). As has been shown in these two previously described PTPs, the novel PTP reported here contains a region 3 prime of the PTP domain which is very rich in proline, serine, and threonine (~29%) (boxed residues in FIG. 1). This region lacks other significant homology with PTPs PEP and PEST, and it is also much shorter in the novel PTP described here. Finally, a short region of 20 amino acids at the very carboxy terminus of the protein is highly homologous to similar carboxy-terminal regions in PTPs PEP and PEST (FIG. 2). This region is rich in basic residues and the homologous area in PTP PEP has been shown to be involved with the localization of this enzyme to the nucleus (Flores et al., supra). However, this region also contains two negatively charged residues (arrowheads in FIG. 2), so it is likely that this novel PTP is a cytoplasmically localized enzyme, as has been demonstrated for PTP PEST (Charest et al., supra). Finally, the novel PTP described here contains a serine residue at position 37 (shown starred in FIG. 2) which is conserved in all three members of this family and which has been shown to be phosphorylated in PTP PEST by protein kinases C and A (Garton and Tonks, *EMBO J.* 13(16), 3763–71 [1994]). Interestingly, increased phosphorylation at this site is inhibitory to the PTPase activity of this PTP (Banville et al., *Genomics* 27(1), 165–173 [1995]). In summary, the novel PTP described here appears to be a new member of a family of non-receptor PTPs which contain P, S and T rich regions (FIG. 3). In addition, all three of these PTPs contain a homologous carboxy-terminal region which has been shown to function as a nuclear localization signal for one of the family members (PTP PEP), although the murine PEST enzyme has been found to localize to the cytoplasm.

Previous analyses of the genomic structures of other PTPs suggested that these enzymes were constructed from genes containing a large number of introns. This appears to be the case for the novel PTP described here as well. As can be seen from FIG. 4, the hematopoietic progenitor cell PTP gene is subdivided by 14 introns. Analysis of the intronic structure of this novel PTP as compared with that found for other PTPs suggests that the novel progenitor cell enzyme is divided into a comparable number of coding exons (for example, Banville et al., supra). In addition, as described below, there appears to be at least one other smaller transcript, as well as a heterogeneous collection of large transcripts, suggesting that alternate splicing may occur in this gene. Finally, chromosomal localization studies have demonstrated that the gene encoding the human form of this PTP is found on chromosome 14 (D. Dowbenko and L. Lasky, unpublished data).

Figure 5:
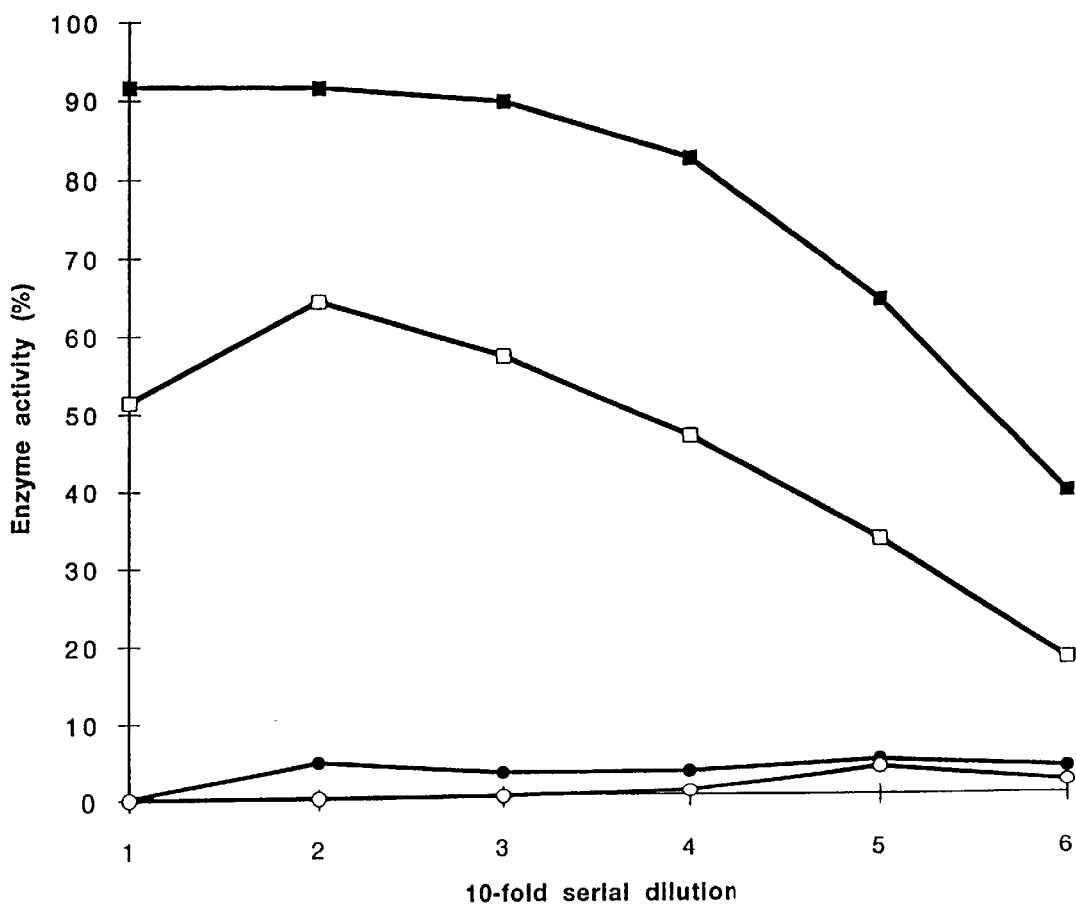
FIG. 5. In vitro tyrosine phosphatase activity of the PTP HSC. Shown is the enzymatic activity obtained using isolated, bacterially produced GST-phosphatase domain of PTP HSC. Black squares, serial dilutions of GST-PTP HSC in the absence of orthovanadate; white squares, enzymatic activity of GST-PTP HSC in the presence of vanadate; closed circle, enzymatic activity of GST alone; open circles enzymatic activity with an inactive GST-PTP (J. Cheng and L. Lasky—unpublished data). The initial undiluted reaction contained 2 µg of each protein.

While the sequence of the N-terminal PTP domain contained many of the conserved amino acids found to be critical for substrate recognition and tyrosine dephosphorylation(Jia et al., supra), it was important to demonstrate that this sequence indeed encoded an active PTP domain. To this end we produced a construct using the glutathione-S-transferase (GST) fusion system which contained the entire PTP-homologous region derived from the novel cDNA clone. The protein was isolated from induced cultures of bacteria, and it was tested for the dephosphorylation of tyrosine using two different phosphorylated peptides (see materials and methods). As can be seen from FIG. 5, the isolated GST-PTP domain fusion protein had a very high level of PTP activity, with significant dephosphorylation at only 20 picograms of enzyme per reaction, which was partially sensitive to inhibition by orthovanadate. The only partial inhibition of enzyme activity by orthovanadate was likely due to the high level of activity as well as insufficient levels of the inhibitor. These data indicate that this hematopoietic progenitor cell PTP is an active tyrosine phosphatase.

C. Expression of the Progenitor Cell PTP Transcript

Figure 6A:
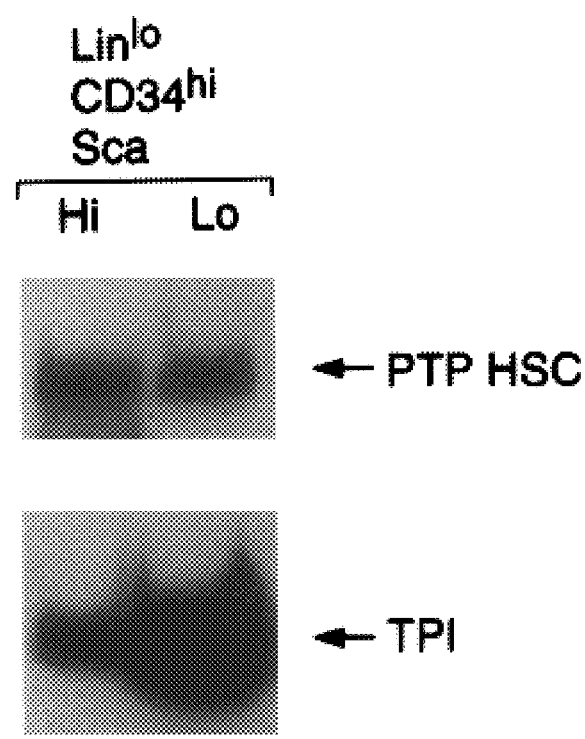
FIGS. 6A and B. PCR analysis of PTP HSC expression. A. $lin^{lo}CD34^{hi}sca^{hi}$ or $lin^{lo}CD34^{hi}sca^{lo}$ hematopoietic progenitor cells were isolated from murine embryos at day 11 of development. RNA was isolated and analyzed by quantitative PCR. The upper band corresponds to the PTP HSC transcript while the lower band corresponds to the triose phosphate isomerase (TPI) internal standard. B. $lin^{lo}CD34^{hi}sca^{hi}$ hematopoietic progenitor/stem cells were purified from murine fetal liver and incubated for up to 14 days in IL-s, IL-s, EPO and GM-CSF. RNA was isolated at various times and analyzed by quantitative PCR as described in A.
Figure 6B:
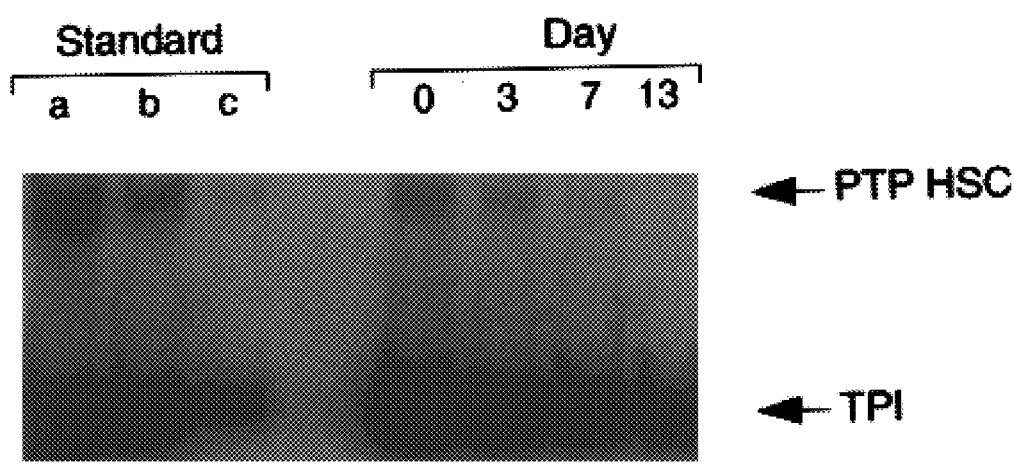

The isolation of the novel PTP from the $lin^{lo}CD34^{hi}sca^{hi}$ population of hematopoietic stem cells suggested that this PTP might be specific for very early progenitor cells. As FIG. 6A illustrates, quantitative PCR comparing the levels of the transcript encoding this PTP in the $lin^{lo}CD34^{hi}sca^{hi}$, a largely undifferentiated population containing hematopoietic stem cells (Spangrude et al., supra Krause et al., supra; Zeigler et al., *Blood* 84(8), 2422–2430 [1994]), versus the $lin^{lo}CD34^{hi}sca^{lo}$ population, a more differentiated cell population (Spangrude et al., supra), containing committed progenitors, demonstrated that there was an approximately 10 fold lower level of the transcript in the more differentiated $sca^{lo}$ cells. In order to examine if this downregulation continued as differentiation progressed, quantitative PCR was performed using RNA isolated from suspension cultures of $lin^{lo}CD34^{hi}sca^{hi}$ cells that were exposed to IL-1, IL-3, EPO and GM-CSF for various periods of time in the absence of stromal cells. Analysis of cell numbers, together with Wright-Giemsa staining of the cultures, revealed that the undifferentiated $lin^{lo}CD34^{hi}sca^{hi}$ cell population dramatically expanded in the presence of these growth and differentiation factors and also metamorphosed along the myeloid pathway to ultimately give rise to cultures that contained predominately macrophages after 14 days (data not shown). As FIG. 6B illustrates, the transcript encoding the novel PTP disappears as the cells replicate and develop, and it is completely absent after approximately 7 days in culture. These data are consistent with a role for this PTP in early stem or progenitor cells, but not in the mature, committed cell populations.

Figure 7A:
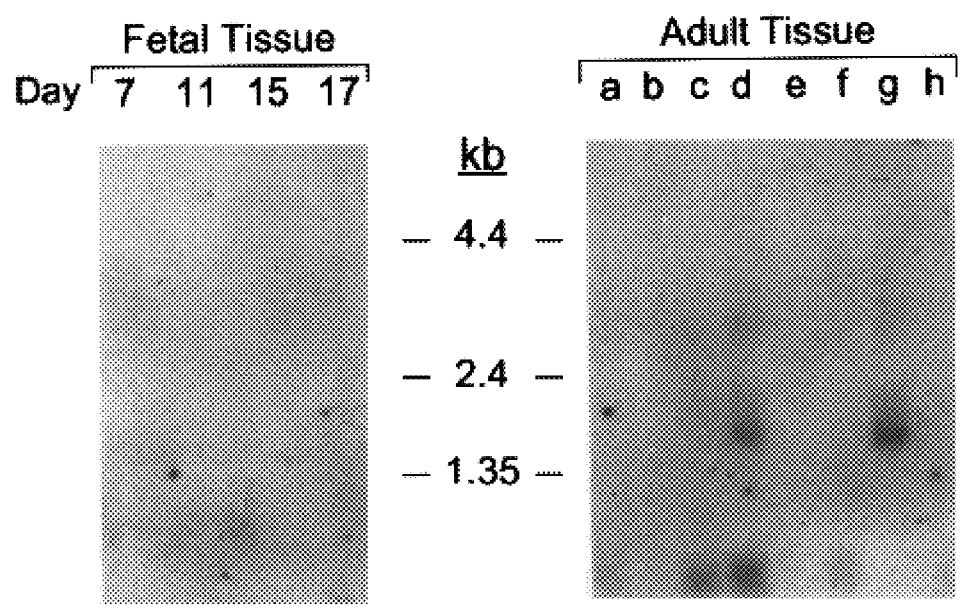
FIGS. 7A, B-1, B-2, and C. PTP HSC Transcript analysis in embryonic and adult tissues and hematopoietic cell lines. A. Illustrated is a tissue northern blot probed with a cDNA encoding PTP HSC. The left panel illustrates RNA isolated from variously aged embryos, while the right panel illustrates RNA isolated from: a. heart, b., brain, c. spleen, d. lung, e. liver, f. skeletal muscle, g. kidney, h. testis. B. Illustrated is a northern blot of RNA isolated from BAF 3 (a), 32D (b) and FDCP (c) hematopoietic progenitor cells (FIG. 7B-1). Also shown is the ethidium bromide stain of the same gel prior to transfer(FIG. 7B-2). C. PCR analysis of RNA isolated from BAF 3 (a), 32 D (b), T cell clone (c), FDCP (d), 11 day embryos (e) and a control with no reverse transcriptase (f).

The potential importance of this PTP specifically to the hematopoietic system is illustrated in FIG. 7A where northern blot analyses of various tissues and cell lines are shown. As can be seen from this figure, the transcript appears to be undetectable in the embryonic samples, and it is expressed at exceedingly low levels in adult lung and kidney. Thus, while there are clearly hematopoietic stem cells in the embryo, they must be so rare as to not allow for the direct detection of the transcript encoding the novel PTP. Particularly interesting is the lack of a signal in the RNA isolated from the adult spleen, a hematopoietic compartment that contains predominately mature, differentiated hematopoietic cells and which was previously shown to express PTP PEP (Matthews et al., supra). The very faint transcripts detected in the lung have been confirmed by non-quantitative PCR analysis (J. Cheng and L. Lasky-unpublished data). However, the transcripts in the lung are very rare and may be aberrant, since screening of an adult lung library ($1 \times 10^6$ clones) resulted in only two positive isolates, both of which contained introns (J. Cheng and L. Lasky—unpublished observations).

Figure 4:
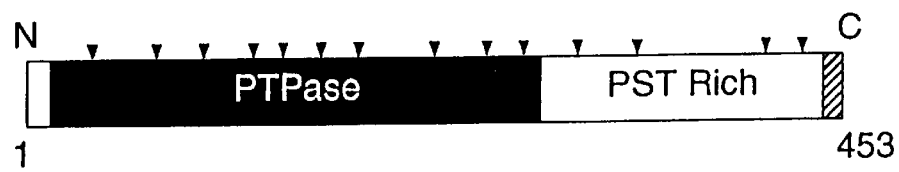
FIG. 4. Intron sites superimposed on the PTP HSC domain structure. Analysis of the gene encoding PTP HSC revealed the location of 14 introns that are shown as triangles in this figure.
Figure 7C:
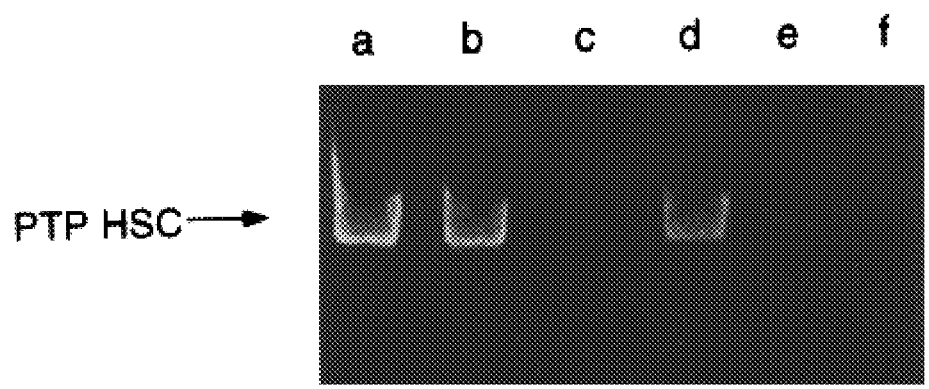
Figures 1, 7B:
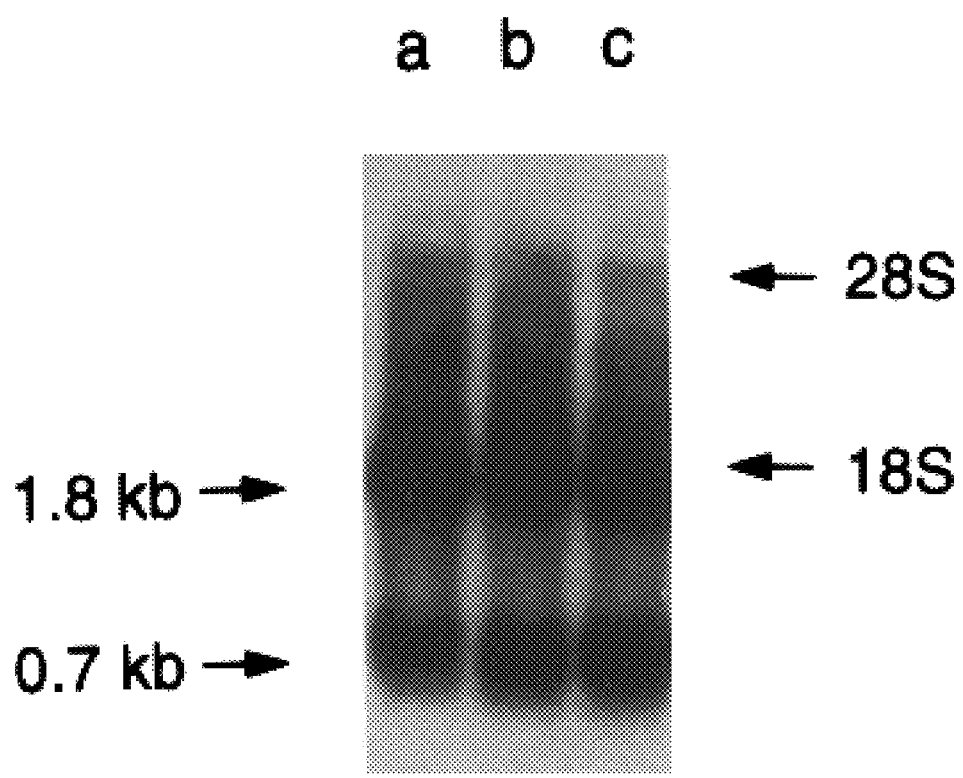
FIGS. 1A and 1B. DNA and deduced protein sequence of the murine PTP HSC cDNA. Illustrated is the DNA sequence (SEQ. ID. NO: 1) and deduced protein sequence (SEQ. ID. NO: 2) of the murine PTP HSC cDNA. The overlined region is the phosphatase homologous domain. The asterisk denotes the active site cysteine residue. The P,S,T-rich region is illustrated by boxes around these residues. The shaded carboxy terminal region is homologous to a nuclear localization signal found on murine PTP PEP (Flores et al., *Mol. Cell. Biol.* 14(7), 4938–46 [1994]).
Figures 2, 7B:
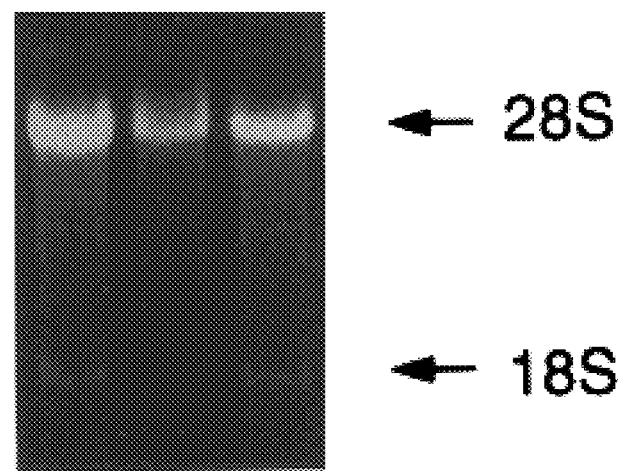
FIGS. 2A and 2B. Sequence homologies of murine PTP HSC, murine PTP PEP, and human PTP PEST. A. The phosphatase domain homologies show that these three proteins are highly related to each other. A star over the residue (amino acid 37 of PTP HSC) illustrates a conserved serine that is phosphorylated by protein kinases A and C and which appears to negatively regulate PTPase activity (Garton and Tonks, *EMBO J.* 13(16), 3763–71 [1994]). The amino acid sequence of positions 24–301 of PTP PEP is shown in SEQ. ID. NO: 18; the amino acid sequence of positions 28–299 of PTP PEST is shown in SEQ. ID. NO: 19. B. A second highly homologous region is found at the carboxy terminus of these three proteins (SEQ. ID. NO: 22 showing amino acids 783–801 of PTP PEP; SEQ. ID. NO: 23 showing amino acids 760–780 of PTP PEST). This region has been shown to confer nuclear localization on PTP PEP. Interestingly PTP PEST is localized to the cytoplasm, and it has been hypothesized that this is due to the two negatively charged residues shown by the arrows. As can be seen, PTP HSC also contains these negatively charged residues, suggesting that it is also localized to the cytoplasm.

The lack of detectable signal in most tissues of the adult and embryo, coupled with the identification of the transcript in the highly purified stem cell population, but not in the differentiated hematopoietic cells, suggested that this PTP might be expressed in hematopoietic progenitor cell lines. As FIG. 7B illustrates, the transcripts encoding this novel PTP are easily detectable in the three different murine hematopoietic progenitor cell lines tested by both northern and PCR analyses. In all three cases, these lines represent relatively undifferentiated precursors of mature hematopoietic cells, although they are certainly not self-renewing stem cells. The cells appear to encode two major transcripts, in addition to a diversity of minor transcripts. One major transcript is an ~1.8 kB RNA that corresponds to the cDNA clone described above, while the other encodes a ~0.7 kB RNA that remains to be characterized. However, it is likely that this smaller transcript is due to alternative splicing, since, as described above, the gene encoding this PTP is divided into a large number of exons (FIG. 4). FIG. 7C illustrates that the PTP HSC transcript is undetectable by PCR in a differentiated T cell clone, a result which is again consistent with the downregulation of this PTP in differentiated cells. Finally, PCR analysis of various human cell lines using the murine primer pair revealed expression of a similarly sized fragment in human CMK progenitor cells, and the sequence of this PCR fragment revealed that the human homologue is highly conserved with the murine PTP (J. Cheng, Kai Wu and L. Lasky-unpublished results). In summary, the novel PTP described here appears to be expressed predominately in very early hematopoietic progenitor cells, consistent with a potential role in the regulation of the differentiation state of these cells.

D. Discussion

The ability of the hematopoietic stem cell to self renew in the absence of differentiation is an important factor which allows for this cell to provide a large number of progeny throughout the lifetime of the organism. The maintenance of the undifferentiated state must occur at the same time as the stem cell replicates, since this cell type must be continually replenished. Thus, there must be specific mechanisms that decrease some aspects of cellular activation, such as differentiation, while not affecting others, such as division. Because tyrosine phosphorylation is a critical aspect of cellular activation, based upon the results disclosed herein, it is likely that distinctive mechanisms which regulate tyrosine phosphorylation are involved with the maintenance of the self renewing stem cell. Such specificity can be accomplished in part by the expression of the appropriate growth factors by the hematopoietic cell stroma. However, another means by which such regulation can occur is by the dephosphorylation of a subset of tyrosine phosphorylated proteins. One mechanism that would allow for specific dephosphorylation is via PTPs which recognize only a fraction of the tyrosine phosphorylated proteins in the cell. Thus, the analysis of PTPs expressed by hematopoietic stem cells might further our understanding of the mechanisms by which stem cell self renewal is attained. The non-receptor PTP described in the present application has some of the features that might be expected for a regulator of stem cell differentiation.

Several aspects of this novel PTP, which is referred to throughout the specification and claims as the PTP of hematopoietic stem cells or PTP HSC, are consistent with a role in the regulation of aspects of early hematopoietic progenitor cell biology. First, the specific expression of the transcript in very early hematopoietic progenitor cells, together with the down-regulation of the message as the cells differentiate, is compatible with a role for this enzyme in physiological aspects of the less differentiated stem cell. While little is understood regarding the regulation of genes in very early hematopoietic progenitor cells, the apparently unique expression of this gene predominately in these comparatively undifferentiated cells suggests that novel mechanisms of transcriptional regulation might be utilized in the control of this locus (Orkin, *Curr. Opin. Cell Biol.* 7(6), 870–877 [1995]). In addition, the predominate lack of expression of this PTP in most adult tissues, with the exception of extremely low levels in the lung and the kidney, is also consistent with a role for this enzyme specifically within the hematopoietic progenitor cell compartment. This is in stark contrast to the expression of PTP PEP, which is found in the lymphoid compartment (Takekawa et al., supra), and PTP PEST, which is apparently ubiquitously expressed in a number of cell lines and tissues (Yang et al., supra). Second, the PTP domain can be thought of as a moderator of cell activation by virtue of its ability to dephosphorylate tyrosine residues. Tyrosine phosphorylation can either up or down-regulate the activities of various proteins (Fantl et al., supra), so that the PTP HSC might activate or inhibit a specific subset of tyrosine phosphorylated proteins. In a cell that requires a down-regulation of differentiation, this type of specific modulation would allow for the control of the phosphotyrosine levels of proteins activated by various growth factors produced by the hematopoietic stroma. Together, these data are compatible with a function for this enzyme in the modulation of development of the stem cell that is induced by the various growth factors produced by the hematopoietic microenvironment.

The hypothesis that PTPs such as PTP HSC are involved with the maintenance of an undifferentiated state in the hematopoietic stem cell suggests possibilities regarding the substrates recognized by this type of PTP. Several of the substrates for the PTPs have been previously characterized. For example, the alpha PTP, a receptor PTP, has been found to regulate the levels of src tyrosine phosphorylation which results in differentiation of neuronal progenitor cells. Lar, as well as CD45, are apparently involved with the regulation of the tyrosine phosphorylation levels of the insulin receptor (Kulas et al., *J. Biol. Chem.* 271(2), 748–754 (1996); Kulas et al., *J. Biol. Chem.* 271(2), 755–760 [1996]). From the standpoint of hematopoiesis, the SH 2 domain containing PTP 1C phosphatase has been shown to be critically involved with the regulation of myeloid development in the motheaten mouse as well as with the activation state of the EPO receptor (Schulz et al., supra; McCulloch (Klingmuller et al., supra). Finally, another SH2-containing PTP, PTP 1D has been found to positively regulate the activity of the prolactin receptor (Ali et al., *EMBO J.* 15(1), 135–142 [1996]). These examples, among others, are consistent with a role for cytoplasmically-localized PTP domains in the regulation of a variety of cellular processes. However, the nature of the substrates recognized by the rarer nuclear PTP family is unknown. The dual specificity (i.e. tyrosine and serine/threonine dephosphorylation) phosphatase encoded by the cdc25 locus is a nuclear enzyme that is critical for the regulation of mitosis (Gautier et al., *Cell* 67(1), 197–211 [1991]). In addition, PAC-1, another nuclear localized PTP, appears to be involved with the regulation of the mitogen activated protein kinases. A recently described dual specificity phosphatase, TYP 1, related to the vaccinia virus VH 1 phosphatase, appears to be involved with the regulation of both the ERK and JNK family of mitogen activated protein kinases (King et al., *Oncogene* 11, 2553–2563 [1995]). These data suggest that several currently described phosphatases appear to play roles in the regulation of tyrosine phosphorylated nuclear proteins.

Another possible substrate for both the nuclear and cytoplasmic PTP enzymes are the STAT proteins. These transcriptional activators encompass a family of at least 6 different members, all of which are activated by the JAK tyrosine kinases (Darnell et al., *Science* 264(5164), 141501421 [1994]; Ihle et al., *Annu Rev. Immunol.* 13, 369–398 [1995]). JAK phosphorylation is stimulated by the formation of receptor complexes that are stimulated by the binding of various hematopoietic and other growth factor-like molecules (Darnell et al., supra). The phosphorylated STAT proteins than dimerize, migrate to the nucleus and bind specifically to various DNA elements that regulate the transcription of growth and differentiation genes (Shuai et al., Science 261(5129). 1744–1746 [1993]; Heim et al., Science 267(5202),1347–49 [1995]). Thus, because these transcription factors are linked with the activation of hematopoietic differentiation factors, they provide appealing targets for negative regulation in hematopoietic stem cells. The absolute requirement for tyrosine phosphorylation of these transcriptional activators thus suggests that the novel PTP reported here could regulate STAT activation via dephosphorylation of tyrosine residues. In this manner, the upregulation of genes specific to the differentiated state could be inhibited by the dephosphorylation of one or more activated STAT molecules. This hypothesis is especially appealing in the case of the hematopoietic stem cells. In this case, the activation of the STAT proteins by the binding of various hematopoietic growth and differentiation factors, a state which would induce terminal differentiation, could be downregulated by a stem cell specific PTP such as PTP HSC. If this hypothesis is correct, the manner by which specific STAT dephosphorylation occurs must be investigated. However, it is possible that the proline, serine, threonine rich domain of PTP HSC might function to bind to only a subset of STATs.

Finally, recent data have shown that PTP PEST can associate with the $p52^{shc}$ and $p66^{shc}$ SH2-containing adaptorproteins in a protein kinase C dependent fashion (Habib et al., J. Biol. Chem. 269(41), 25243–25246 [1994]). This association was through an interaction between the N-terminal region of SHC and the carboxy-terminal P,S,T rich region of the PTP PEST. The fact that this association was enhanced by protein kinase C suggested that serine or threonine phosphorylation might be involved, and a serine in the P,S,T rich region of PTP PEST is known to be phosphorylated by protein kinase C (Garton and Tonka, supra). Interestingly, carbachol, an activator of G protein coupled signaling, was also able to stimulate this association, suggesting that PTP PEST may be involved with the cross talk between G coupled and tyrosine kinase pathways. Because of the similarity of PTP HSC to PTP PEST, we suggest that the novel hematopoietic cell PTP of the present invention may also interact with SHC, and we are currently examining this possibility using the yeast two hybrid system.

In summary, the data disclosed in this example suggest that hematopoietic stem/progenitor cells specifically express a PTP which appears to be downregulated as the cells differentiate. The PTP seems to be predominately specific to hematopoietic progenitor cells, suggesting an important role in the development of this cell compartment. However, while these data are potentially important, a number of studies remain to be accomplished. Thus, the possibility that the STATs are substrates for this enzyme, the possible interaction of the enzyme with SHC, the constitutive expression of the enzyme in transfected cells and in transgenic animals, and the effects of null mutations at this locus in vivo may provide for further insights into the mechanisms by which stem cell self renewal is regulated.

EXAMPLE 2

Cloning of a Human PTP HSC

Two oligonucleotides (sense: 5'ACTTGGTGAGGAGCT-TCTTGGAGCAGCTGGAGG3' (SEQ. ID. NO: 20), and antisense: 5'GGAATGTAACCTGGAGGGTCCTGA3' (SEQ. ID. NO: 21)) were used as PCR primers with reverse transcribed RNA isolated from human CMK hematopoietic progenitor cells. The conditions for PCR were identical to those described in Example 1 for the isolation of the PCR fragment encoding murine PTP HSC. The PCR fragment was subcloned into pBS (Bluescript) plasmid, and the DNA sequence was determined as described for the murine sequence in Example 1. The partial nucleotide sequence and deduced amino acid sequence of the human PTP HSC are shown in FIGS. 8A and 8B.

EXAMPLE 3

Expression of the Murine and Human PTP HSC

The native murine PTP HSC polypeptides are expressed in mammalian cells using standard techniques. Briefly, a DNA fragment encoding the entire PTP HSC is ligated into an expression vector (e.g. PRK5). The expression vector is then transfected into mammalian cells (e.g. embryonic kidney 292 cells), and the protein expression is determined using a monoclonal or polyclonal antibody directed against the native PTP HSC to be expressed.

All documents cited throughout this application as well as the documents cited therein are hereby expressly incorporated by reference.

What is claimed is:

1. An isolated non-receptor protein tyrosine phosphatase of hematopoietic stem cells (PTP HSC), comprising the amino acid sequence of SEQ ID NO: 2 or SEQ ID NO: 17.

2. The PTP HSC of claim of claim 1 which is human, and comprises the amino acid sequence of SEQ ID NO: 17.

3. A method for the expansion of undifferentiated stem cells in cell culture, comprising (a) adding to said cell culture a PTP HSC of claim 1, and (b) cultivating said undifferentiated stem cells.

* * * * *

SEQUENCE LISTING

```
<160> NUMBER OF SEQ ID NOS:  23

<210> SEQ ID NO 1
<211> LENGTH: 1529
<212> TYPE: DNA
<213> ORGANISM: Mus musculus

<400> SEQUENCE: 1
ctcagagcgg gtcgcagcat gagtcgccat acggacttgg tgaggagctt          50
cttggagcag ctggaggccc gggactaccg ggaggggggca atcttcgttc         100 gtgagttcag cgacattaag gcccgctcag tggcctggaa gtctgaaggt         150
gtgtgttcca ctaaagccgg cagtcggctt gggaacacga acaagaaccg         200
```

-continued

| | |
|---|---|
| ctacaaagat gtggtagcat atgatgagac aagagtcatc ctttccctgc | 250 |
| tccaagagga gggacatgga aattacatca atgccaactt catccggggc | 300 |
| atagatggaa gccaggccta cattgcgacg caaggacccc tgcctcacac | 350 |
| actgttggac ttctggcgcc tggtttggga gtttggggtc aaggtaatcc | 400 |
| tgatggcctg tcaagagaca gaaaatggac ggaggaagtg tgaacgctat | 450 |
| tgggcccggg agcaggagcc tctaaaggct gggcctttct gcatcaccct | 500 |
| gacaaaggag acaacactga atgcagacat cactctcagg accctccagg | 550 |
| ttacattcca gaaggaattc cgctctgtgc accaactaca gtatatgtcc | 600 |
| tggccagacc acggggttcc cagcagttct gatcacattc tcaccatggt | 650 |
| ggaggaggcc cgctgcctcc aagggcttgg acctggaccc ctctgtgtcc | 700 |
| actgcagtgc tggctgcgga cgaacaggtg tcctgtgcgc tgttgactat | 750 |
| gtgaggcagt tgctgctgac ccagacaatc cctcccaact tcagtctctt | 800 |
| ccaagtggtc ctggagatgc ggaaacagcg cctgcagca gtgcagacag | 850 |
| aggagcagta caggttcctg taccacacag tggctcagct attctcccgc | 900 |
| actctccagg acaccagccc ccaataccag aacctcaagg agaactgcgc | 950 |
| tccaatctgc aaggaagctt tctccctcag gacctcctca gccctgcctg | 1000 |
| ccacatcccg gccaccagga ggggttctca ggagcatctc ggtgcctgcg | 1050 |
| cccccgaccc tccccatggc tgacacttac gctgtggtgc agaagcgtgg | 1100 |
| cgcttcggcg ggcacagggc cggggccgcg ggcgcccacc agcacggaca | 1150 |
| ccccgattta cagccaggtg gctccacgtg cccagcgacc ggtggcacac | 1200 |
| acggaggacg cacaggggac aacggcactg cgccgagttc ctgcggacca | 1250 |
| aaactcttcc gggcctgatg cctacgaaga agtaacagat ggagcacaga | 1300 |
| ctggagggct aggcttcaac ttgcgcatcg gaaggcccaa agggccccgg | 1350 |
| gatcctccag cagagtggac acgggtgtaa cgagtgctgt gccagttata | 1400 |
| gcctgccact cggtggtggc tggactcctg gaaccaccat actgctgtgc | 1450 |
| agtgtgttat gtatgagtgg gacttgtggg cctgattcaa aataaaagtt | 1500 |
| tctcagggcg aaaaaaaaa aaaaaaaa | 1529 |

<210> SEQ ID NO 2
<211> LENGTH: 453
<212> TYPE: PRT
<213> ORGANISM: Mus Musculus

<400> SEQUENCE: 2

```
Met Ser Arg His Thr Asp Leu Val Arg Ser Phe Leu Glu Gln Leu
  1               5                  10                  15

Glu Ala Arg Asp Tyr Arg Glu Gly Ala Ile Phe Val Arg Glu Phe
                 20                  25                  30

Ser Asp Ile Lys Ala Arg Ser Val Ala Trp Lys Ser Glu Gly Val
                 35                  40                  45

Cys Ser Thr Lys Ala Gly Ser Arg Leu Gly Asn Thr Asn Lys Asn
                 50                  55                  60

Arg Tyr Lys Asp Val Val Ala Tyr Asp Glu Thr Arg Val Ile Leu
                 65                  70                  75

Ser Leu Leu Gln Glu Glu Gly His Gly Asn Tyr Ile Asn Ala Asn
                 80                  85                  90
```

```
Phe Ile Arg Gly Ile Asp Gly Ser Gln Ala Tyr Ile Ala Thr Gln
             95                 100                 105

Gly Pro Leu Pro His Thr Leu Leu Asp Phe Trp Arg Leu Val Trp
        110                 115                 120

Glu Phe Gly Val Lys Val Ile Leu Met Ala Cys Gln Glu Thr Glu
            125                 130                 135

Asn Gly Arg Arg Lys Cys Glu Arg Tyr Trp Ala Arg Glu Gln Glu
        140                 145                 150

Pro Leu Lys Ala Gly Pro Phe Cys Ile Thr Leu Thr Lys Glu Thr
            155                 160                 165

Thr Leu Asn Ala Asp Ile Thr Leu Arg Thr Leu Gln Val Thr Phe
        170                 175                 180

Gln Lys Glu Phe Arg Ser Val His Gln Leu Gln Tyr Met Ser Trp
            185                 190                 195

Pro Asp His Gly Val Pro Ser Ser Ser Asp His Ile Leu Thr Met
        200                 205                 210

Val Glu Glu Ala Arg Cys Leu Gln Gly Leu Gly Pro Gly Pro Leu
            215                 220                 225

Cys Val His Cys Ser Ala Gly Cys Gly Arg Thr Gly Val Leu Cys
        230                 235                 240

Ala Val Asp Tyr Val Arg Gln Leu Leu Leu Thr Gln Thr Ile Pro
            245                 250                 255

Pro Asn Phe Ser Leu Phe Gln Val Val Leu Glu Met Arg Lys Gln
        260                 265                 270

Arg Pro Ala Ala Val Gln Thr Glu Glu Gln Tyr Arg Phe Leu Tyr
            275                 280                 285

His Thr Val Ala Gln Leu Phe Ser Arg Thr Leu Gln Asp Thr Ser
        290                 295                 300

Pro His Tyr Gln Asn Leu Lys Glu Asn Cys Ala Pro Ile Cys Lys
        305                 310                 315

Glu Ala Phe Ser Leu Arg Thr Ser Ser Ala Leu Pro Ala Thr Ser
        320                 325                 330

Arg Pro Pro Gly Gly Val Leu Arg Ser Ile Ser Val Pro Ala Pro
        335                 340                 345

Pro Thr Leu Pro Met Ala Asp Thr Tyr Ala Val Val Gln Lys Arg
        350                 355                 360

Gly Ala Ser Ala Gly Thr Gly Pro Gly Pro Arg Ala Pro Thr Ser
        365                 370                 375

Thr Asp Thr Pro Ile Tyr Ser Gln Val Ala Pro Arg Ala Gln Arg
        380                 385                 390

Pro Val Ala His Thr Glu Asp Ala Gln Gly Thr Thr Ala Leu Arg
        395                 400                 405

Arg Val Pro Ala Asp Gln Asn Ser Ser Gly Pro Asp Ala Tyr Glu
        410                 415                 420

Glu Val Thr Asp Gly Ala Gln Thr Gly Gly Leu Gly Phe Asn Leu
        425                 430                 435

Arg Ile Gly Arg Pro Lys Gly Pro Arg Asp Pro Pro Ala Glu Trp
        440                 445                 450

Thr Arg Val

<210> SEQ ID NO 3
<211> LENGTH: 39
<212> TYPE: DNA
```

```
<213> ORGANISM: Artificial Sequence
<220> FEATURE:
<223> OTHER INFORMATION: Synthetic oligonucleotide probe

<400> SEQUENCE: 3
cacggtcgac ggtgaggagc ttctttgagc agctggagg                              39

<210> SEQ ID NO 4
<211> LENGTH: 42
<212> TYPE: DNA
<213> ORGANISM: Artificial Sequence
<220> FEATURE:
<223> OTHER INFORMATION: Synthetic oligonucleotide probe

<400> SEQUENCE: 4
gttgcggccg cgattggagc gcagttctcc ttgaggttct gg                          42

<210> SEQ ID NO 5
<211> LENGTH: 36
<212> TYPE: DNA
<213> ORGANISM: Artificial Sequence
<220> FEATURE:
<223> OTHER INFORMATION: Synthetic oligonucleotide probe

<400> SEQUENCE: 5
cctggagggt cctgagagtg atgtctgcat tcagtg                                 36

<210> SEQ ID NO 6
<211> LENGTH: 34
<212> TYPE: DNA
<213> ORGANISM: Artificial Sequence
<220> FEATURE:
<223> OTHER INFORMATION: Synthetic oligonucleotide probe

<400> SEQUENCE: 6
cctcttggag cagggaaagg atgactcttg tctc                                   34

<210> SEQ ID NO 7
<211> LENGTH: 30
<212> TYPE: DNA
<213> ORGANISM: Artificial Sequence
<220> FEATURE:
<223> OTHER INFORMATION: Synthetic oligonucleotide probe

<400> SEQUENCE: 7
cagctgctcc aagaagctcc tcaccaagtc                                        30

<210> SEQ ID NO 8
<211> LENGTH: 31
<212> TYPE: DNA
<213> ORGANISM: Artificial Sequence
<220> FEATURE:
<223> OTHER INFORMATION: Synthetic oligonucleotide probe

<400> SEQUENCE: 8
ggtagaggtg ggcagggtga agtgttctcg c                                      31

<210> SEQ ID NO 9
<211> LENGTH: 36
<212> TYPE: DNA
<213> ORGANISM: Artificial Sequence
<220> FEATURE:
<223> OTHER INFORMATION: Synthetic oligonucleotide probe

<400> SEQUENCE: 9
cactgaatgc agacatcact ctcaggaccc tccagg                                 36
```

```
<210> SEQ ID NO 10
<211> LENGTH: 34
<212> TYPE: DNA
<213> ORGANISM: Artificial Sequence
<220> FEATURE:
<223> OTHER INFORMATION: Synthetic oligonucleotide probe

<400> SEQUENCE: 10
gagacaagag tcatcctttc cctgctccaa gagg                             34

<210> SEQ ID NO 11
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 11
gaatggtaac ctggagggtc ctgag                                       25

<210> SEQ ID NO 12
<211> LENGTH: 18
<212> TYPE: DNA
<213> ORGANISM: Artificial Sequence
<220> FEATURE:
<223> OTHER INFORMATION: Synthetic oligonucleotide probe

<400> SEQUENCE: 12
gagaaggtcg tgttcgag                                               18

<210> SEQ ID NO 13
<211> LENGTH: 18
<212> TYPE: DNA
<213> ORGANISM: Artificial Sequence
<220> FEATURE:
<223> OTHER INFORMATION: Synthetic oligonucleotide probe

<400> SEQUENCE: 13
gtgtacttcc tgtgcctg                                               18

<210> SEQ ID NO 14
<211> LENGTH: 18
<212> TYPE: DNA
<213> ORGANISM: Artificial Sequence
<220> FEATURE:
<223> OTHER INFORMATION: Synthetic oligonucleotide probe
<221> NAME/KEY: unsure
<222> LOCATION: 2, 5, 9, 14
<223> OTHER INFORMATION: unknown base

<400> SEQUENCE: 14
anttntggng atgnttgg 18

<210> SEQ ID NO 15
<211> LENGTH: 15
<212> TYPE: DNA
<213> ORGANISM: Artificial Sequence
<220> FEATURE:
<223> OTHER INFORMATION: Synthetic oligonucleotide probe
<221> NAME/KEY: unsure
<222> LOCATION: 5-8
<223> OTHER INFORMATION: unknown base

<400> SEQUENCE: 15
ggacnnnntc ggcca                                                  15
```

<210> SEQ ID NO 16
<211> LENGTH: 466
<212> TYPE: DNA
<213> ORGANISM: Homo Sapien

<400> SEQUENCE: 16

| gcgcggggcg | gccgggaggg | ggcagtcctc | gccggcgagt | tcagcgacat | 50 |
| ccaggcctgc | tcggccgcct | ggaaggctga | cggcgtgtgc | tccaccgtgg | 100 |
| ccggcagtcg | gccagagaac | gtgaggaaga | accgctacaa | agacgtgctg | 150 |
| ccttatgatc | agacgcgagt | aatcctctcc | ctgctccagg | aagagggaca | 200 |
| cagcgactac | attaatggca | acttcatccg | gggcgtggat | ggaagcctgg | 250 |
| cctacattgc | cacgcaagga | cccttgcctc | acaccctgct | agacttctgg | 300 |
| agactggtct | gggagtttgg | ggtcaaggtg | atcctgatgg | cctgtcgaga | 350 |
| gatagagaat | gggcggaaaa | ggtgtgagcg | gtactgggcc | caggagcagg | 400 |
| agccactgca | gactgggctt | ttctgcatca | ctctgataaa | ggagaagtgg | 450 |
| ctgaatgagg | acatca | | | | 466 |

<210> SEQ ID NO 17
<211> LENGTH: 155
<212> TYPE: PRT
<213> ORGANISM: Homo Sapien

<400> SEQUENCE: 17

Ala Arg Gly Gly Arg Glu Gly Ala Val Leu Ala Gly Glu Phe Ser
 1               5                  10                  15
Asp Ile Gln Ala Cys Ser Ala Ala Trp Lys Ala Asp Gly Val Cys
                20                  25                  30
Ser Thr Val Ala Gly Ser Arg Pro Glu Asn Val Arg Lys Asn Arg
                35                  40                  45
Tyr Lys Asp Val Leu Pro Tyr Asp Gln Thr Arg Val Ile Leu Ser
                50                  55                  60
Leu Leu Gln Glu Glu Gly His Ser Asp Tyr Ile Asn Gly Asn Phe
                65                  70                  75
Ile Arg Gly Val Asp Gly Ser Leu Ala Tyr Ile Ala Thr Gln Gly
                80                  85                  90
Pro Leu Pro His Thr Leu Leu Asp Phe Trp Arg Leu Val Trp Glu
                95                  100                 105
Phe Gly Val Lys Val Ile Leu Met Ala Cys Arg Glu Ile Glu Asn
                110                 115                 120
Gly Arg Lys Arg Cys Glu Arg Tyr Trp Ala Gln Glu Gln Glu Pro
                125                 130                 135
Leu Gln Thr Gly Leu Phe Cys Ile Thr Leu Ile Lys Glu Lys Trp
                140                 145                 150
Leu Asn Glu Asp Ile
                155

<210> SEQ ID NO 18
<211> LENGTH: 278
<212> TYPE: PRT
<213> ORGANISM: Homo Sapien

<400> SEQUENCE: 18

Phe Ala Ser Glu Phe Leu Lys Leu Lys Arg Gln Ser Thr Lys Tyr
 1               5                  10                  15

-continued

```
Lys Ala Asp Lys Ile Tyr Pro Thr Thr Val Ala Gln Arg Pro Lys
             20                  25                  30

Asn Ile Lys Lys Asn Arg Tyr Lys Asp Ile Leu Pro Tyr Asp His
             35                  40                  45

Ser Leu Val Glu Leu Ser Leu Thr Ser Asp Glu Asp Ser Ser
             50                  55                  60

Tyr Ile Asn Ala Ser Phe Ile Lys Gly Val Tyr Gly Pro Lys Ala
             65                  70                  75

Tyr Ile Ala Thr Gln Gly Pro Leu Ser Thr Thr Leu Leu Asp Phe
             80                  85                  90

Trp Arg Met Ile Trp Glu Tyr Arg Ile Leu Val Ile Val Met Ala
             95                 100                 105

Cys Met Glu Phe Glu Met Gly Lys Lys Cys Glu Arg Tyr Trp
            110                 115                 120

Ala Glu Pro Gly Glu Thr Gln Leu Gln Phe Gly Pro Phe Ser Ile
            125                 130                 135

Ser Cys Glu Ala Glu Lys Lys Lys Ser Asp Tyr Lys Ile Arg Thr
            140                 145                 150

Leu Lys Ala Lys Phe Asn Asn Glu Thr Arg Ile Ile Tyr Gln Phe
            155                 160                 165

His Tyr Lys Asn Trp Pro Asp His Asp Val Pro Ser Ser Ile Asp
            170                 175                 180

Pro Ile Leu Gln Leu Ile Trp Asp Met Arg Cys Tyr Gln Glu Asp
            185                 190                 195

Asp Cys Val Pro Ile Cys Ile His Cys Ser Ala Gly Cys Gly Arg
            200                 205                 210

Thr Gly Val Ile Cys Ala Val Asp Tyr Thr Trp Met Leu Leu Lys
            215                 220                 225

Asp Gly Ile Ile Pro Lys Asn Phe Ser Val Phe Asn Leu Ile Gln
            230                 235                 240

Glu Met Arg Thr Gln Arg Pro Ser Leu Val Gln Thr Gln Glu Gln
            245                 250                 255

Tyr Glu Leu Val Tyr Ser Ala Val Leu Glu Leu Phe Lys Arg His
            260                 265                 270

Met Asp Val Ile Ser Asp Asn His
            275

<210> SEQ ID NO 19
<211> LENGTH: 272
<212> TYPE: PRT
<213> ORGANISM: Homo Sapien

<400> SEQUENCE: 19

Phe Ala Arg Asp Phe Met Arg Leu Arg Arg Leu Ser Thr Lys Tyr
 1               5                  10                  15

Arg Thr Glu Lys Ile Tyr Pro Thr Ala Thr Gly Glu Lys Glu Glu
             20                  25                  30

Asn Val Lys Lys Asn Arg Tyr Lys Asp Ile Leu Pro Phe Asp His
             35                  40                  45

Ser Arg Val Lys Leu Thr Leu Lys Thr Pro Ser Gln Asp Ser Asp
             50                  55                  60

Tyr Ile Asn Ala Asn Phe Ile Lys Gly Val Tyr Gly Pro Lys Ala
             65                  70                  75

Tyr Val Ala Thr Gln Gly Pro Leu Ala Asn Thr Val Ile Asp Phe
```

```
              80                  85                  90
Trp Arg Met Val Trp Glu Tyr Asn Val Ile Ile Val Met Ala
                 95                 100                 105
Cys Arg Glu Phe Glu Met Gly Arg Lys Lys Cys Glu Arg Tyr Trp
            110                 115                 120
Pro Leu Tyr Gly Glu Asp Pro Ile Thr Phe Ala Pro Phe Lys Ile
            125                 130                 135
Ser Cys Glu Asp Glu Gln Ala Arg Thr Asp Tyr Phe Ile Arg Thr
            140                 145                 150
Leu Leu Leu Glu Phe Gln Asn Glu Ser Arg Arg Leu Tyr Gln Phe
            155                 160                 165
His Tyr Val Asn Trp Pro Asp His Asp Val Pro Ser Ser Phe Asp
            170                 175                 180
Ser Ile Leu Asp Met Ile Ser Leu Met Arg Lys Tyr Gln Glu His
            185                 190                 195
Glu Asp Val Pro Ile Cys Ile His Cys Ser Ala Gly Cys Gly Arg
            200                 205                 210
Thr Gly Ala Ile Cys Ala Ile Asp Tyr Thr Trp Asn Leu Leu Lys
            215                 220                 225
Ala Gly Lys Ile Pro Glu Glu Phe Asn Val Phe Asn Leu Ile Gln
            230                 235                 240
Glu Met Arg Thr Gln Arg His Ser Ala Val Gln Thr Lys Glu Gln
            245                 250                 255
Tyr Glu Leu Val His Arg Ala Ile Ala Gln Leu Phe Glu Lys Gln
            260                 265                 270
Leu Gln
```

<210> SEQ ID NO 20
<211> LENGTH: 33
<212> TYPE: DNA
<213> ORGANISM: Artificial Sequence
<220> FEATURE:
<223> OTHER INFORMATION: Synthetic oligonucleotide probe

<400> SEQUENCE: 20
acttggtgag gagcttcttg gagcagctgg agg            33

<210> SEQ ID NO 21
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 21
ggaatgtaac ctggagggtc ctga            24

<210> SEQ ID NO 22
<211> LENGTH: 19
<212> TYPE: PRT
<213> ORGANISM: Artificial Sequence
<220> FEATURE:
<223> OTHER INFORMATION: Synthetic oligonucleotide probe

<400> SEQUENCE: 22

```
Gly Phe Gly Asn Arg Phe Ser Lys Pro Lys Gly Pro Arg Asn Pro
  1               5                  10                  15
Pro Ser Ala Trp
```

```
<210> SEQ ID NO 23
<211> LENGTH: 21
<212> TYPE: PRT
<213> ORGANISM: Artificial Sequence
<220> FEATURE:
<223> OTHER INFORMATION: Synthetic oligonucleotide probe

<400> SEQUENCE: 23

Ile Gly Phe Gly Asn Arg Cys Gly Lys Pro Lys Gly Pro Arg Asp
 1               5                  10                  15

Pro Pro Ser Glu Trp Thr
                20
```